United States Patent [19]
Bidney et al.

[11] Patent Number: 6,166,291
[45] Date of Patent: Dec. 26, 2000

[54] PRODUCTION OF PATHOGEN RESISTANT PLANTS

[75] Inventors: Dennis L. Bidney, Urbandale; Christopher J. Scelonge, Des Moines, both of Iowa; David G. Charne, Guelph, Canada; Mark K. Mancl, Davis, Calif.; Igor Falak, Georgetown; Katherine A. P. Nazarian, Mississauga, both of Canada; Glenn S. Cole, Woodland, Calif.

[73] Assignee: Pioneer Hi-Bred International, Inc., Des Moines, Iowa

[21] Appl. No.: 09/115,488

[22] Filed: Jul. 14, 1998

Related U.S. Application Data

[60] Provisional application No. 60/053,125, Jul. 18, 1997.

[51] Int. Cl.[7] .............................. C12N 5/04; C12N 15/82; C12N 15/87; A01H 5/00; A01H 1/00
[52] U.S. Cl. .......................... 800/279; 435/468; 435/410; 435/419; 800/278; 800/298; 800/295; 800/301; 800/260; 800/265; 800/306; 800/312; 800/320; 800/320.1; 800/320.2; 800/320.3; 800/322
[58] Field of Search ................................... 435/410, 419, 435/468; 800/278, 279, 295, 306, 298, 312, 301, 320–320.3, 260, 322, 265

[56] References Cited

U.S. PATENT DOCUMENTS

| | | | |
|---|---|---|---|
| 5,362,864 | 11/1994 | Chua | 800/298 |
| 5,516,671 | 5/1996 | Lawrence et al. | 800/279 |
| 5,547,870 | 8/1996 | Datta et al. | 435/418 |

FOREIGN PATENT DOCUMENTS

| | | |
|---|---|---|
| 0818138A1 | 3/1996 | European Pat. Off. . |
| 0891702A1 | 12/1996 | European Pat. Off. . |
| WO 92/14824 | 9/1992 | WIPO . |
| WO 92/15685 | 9/1992 | WIPO . |
| WO 94/12622 | 6/1994 | WIPO . |
| WO 94/13790 | 6/1994 | WIPO . |
| WO 95/12304 | 5/1995 | WIPO . |
| WO 95/14784 | 6/1995 | WIPO . |
| WO 95/21924 | 8/1995 | WIPO . |
| WO 96/31597 | 10/1996 | WIPO . |

OTHER PUBLICATIONS

Lamb and Dixon, (1997). Ann. Rev. Physiol. Plant Mol. Biol., 48: 251–275, "The Oxidative Burst in Plant Disease Resistance".

Zhou, et al., (1997). Analytical Biochemistry 253, 162–168, "A Stable Nonfluorescent Derivative of Resorufin for the Fluorometric Determination of Trace Hydrogen Peroxide: Applications in Detecting the Activity of Phagocyte NADPH Oxidase and Other Oxidases".

Doke, et al., (1996). Gene, 179: 45–51, "The oxidative burst protects plants against pathogen attack: mechanism and role as an emergency signal for plant bio–defence—a review".

Wu, et al., (1995). Plant Cell, 7: 1357–1368, "Disease Resistance Conferred by Expression of a Gene Encoding $H_2O_2$–Generating Glucose Oxidase in Transgenic Potato Plants".

Campbell, et al., (1995). The American Phytopathological Society 79(10): 1039–1045, "Evaluation of Corn Genotypes for Resistance to Aspergillus Ear Rot, Kernel Infection, and Aflatoxin Production".

Campbell, et al., (1995). Phytopathology 85(8): 886–896, "Inheritance of Resistance to Aspergillus Ear Rot and Aflatoxin in Corn Genotypes".

Dumas, et al., (1995). Plant Physiol., 107: 1091–1096, "Tissue–Specific Expression of Germin–Like Oxalate Oxidase during Development and Fungal Infection of Barley Seedlings".

Chen, et al., (1993). Science, 262: 1883–1886, "Active Oxygen Species in the Induction of Plant Systemic Acquired Resistance by Salicyclic Acid".

McPherson, et al., (1992) J. of Biol. Chem., 267(12): 8146–8152, "Galactose Oxidase of Dactylium dendroides".

Mouly, et al., (1992). Plant Science, 85: 51–59, "Differential accumulation of hydroxyproline–rich glycoprotein transcripts in sunflower plants infected with *Sclerotinia sclerotiorum* or treated with oxalic acid".

Devlin, et al., (1992). Plant Physiol., 100: 1189–1195, "Involvement of the Oxidative Burst in Phytoalexin Accumulation and the Hypersensitive Reaction".

Lane, et al., (1991). J. of Biol. Chem., 266(16): 10461–10469, "Homologies between Members of the Germin Gene Family in Hexaploid Wheat and Similarities between These Wheat Germins and Certain Physarum Spherulins".

Mehta and Datta (1991). J. Biol. Chem., 266: 23548–23553, "Oxalate Decarboxylase from*Collybia Velutipes*".

Drawtewka–Kos, et al. (1991). J. Biol. Chem., 264(9): 4896–4900, "Polypeptide Structure of Germin as Deduced from cDNA Sequencing".

(List continued on next page.)

*Primary Examiner*—David T. Fox
*Assistant Examiner*—Ousama M-Faiz Zaghmout

[57] ABSTRACT

Methods for increasing resistance in plants to pathogens by the expression of a hydrogen peroxide/reactive oxygen species producing enzyme or an oxalate degrading enzyme. The present invention relates to a method of producing a pathogen resistant hybrid plant by crossing the appropriate transgenic expressing a hydrogen peroxide/reactive oxygen species producing enzyme or an oxalate degrading enzyme with pathogen tolerant lines or inbreds obtained through conventional genetic manipulations, or by transformation of tolerant plants or plant tissues with a hydrogen peroxide/reactive oxygen species producing gene or by altering the expression of an endogenase hydrogen peroxide/reactive oxygen species producing gene. The synergistic effect of expression of a hydrogen peroxide/reactive oxygen species producing enzyme or an oxalate degrading enzyme in a tolerant background gives significant and unexpectedly high resistance to the pathogens.

4 Claims, 15 Drawing Sheets

OTHER PUBLICATIONS

Godoy, et al., (1990). Physiological Plant Pathology, 37: 179–191, "Use of mutants to demonstrate the role of oxalic acid in pathogenicity of *Sclerotinia sclerotiorum* on *Phaseolus vulgaris*".

Schweizer, et al. (1989). Plant Molec. Biol., 12: 643–654, "cDNA cloning, in vitro transcription and partial sequence analysis of mRNAs from winter wheat (*Triticum aestivum* L.) with induced resistance to *Erysiphe graminis* f. sp. *tritici*".

Apostol, et al. (1989). Plant Phys., 90: 109–116, "Rapid Stimulation of an Oxidative Burst during Elicitation of Cultured Plant Cells".

Newman, et al., (1987). Ann. Appl. Biol. 110 (Supplement), 8: 150–157, "Screening for Resistance to *Sclerotinia Sclerotiorum* in Oilseed Rape in the Glasshouse".

Tressel, et al., (1982). Meth Enzymol, 90: 163–171, "Galactose Oxidase from *Dactylium dendroides*".

Noyes and Hancock, (1981). Physiological Plant Pathology, 18: 123–132, "Role of oxalic acid in the Sclerotinia wilt of sunflower".

Haugaard, et al. (1981). Analytical Biochemistry 116: 341–343, "Use of N–Ethylimaleimide to Prevent Interference by Sulfhydryl Reagents with the Glucose Oxidase Assay for Glucose".

Suigura, et al., (1979). Chem. Pharm. Bull., 27(9): 2003–2007, "Purification and Properties of Oxalate Oxidase from Barley Seedlings".

Kritzman, et al. (1977). Experimental Mycology 1, 280–285, "The Role of Oxalic Acid in the Pathogenic Behavior of *Sclerotium rolfsii* Sacc".

Kritzman, et al. (1976). Journal of General Microbiology 95, 78–86, "Metabolism of $_L$–Threonine and its Relationship to Sclerotium Formation in *Sclerotium rolfsii*".

Maxwell, (1973). Physiological Plant Pathology, 3(2): 279–288, "Oxalate formation in *Whetzelinia sclerotiorum* by oxaloacetate acetylhydrolase".

Neuenschwander, et al. 1995. Is hydrogen peroxide a second messenger of salicylic acid in systemic acquired resistance?. Plant J., 8(2): 227–233.

Zhang, et al.. 1995. Germin–like oxalate oxidase, a $H_2O_2$–producing enzyme, accumulates in barley attacked by the powdery mildew fungus. Plant J., 8(1): 139–145.

Hurkman and Tanaka. 1996. Germin Gene Expression Is Induced in Wheat Leaves by Powdery Mildew Infection. Plant Physiol., 111:735–739.

Lagrimini, et al. 1993. Peroxidase Overproduction in Tomato: Wound–induced Polyphenol Deposition and Disease Resistance. Hortscience, 28(3): 218–221.

Lagrimini, et al. 1992. Expression of a Chimeric Tobacco Peroxidase Gene in Transgenic Tomato Plants. J. Amer. Soc. Hort. Sci, 117(6): 1012–1016.

L. Mark Lagrimini 1991. Wound–Induced Deposition of Polyphenols in Transgenic Plants Overexpressing Peroxidase. Plant Phys, 96: 577–583.

Lagrimini, et al. 1990. Peroxidase–Induced Wilting in Transgenic Tobacco Plants. Plant Cell, (2) 7–18.

Derwent. 1996. WO9629857. A method for creating a salt tolerant and/or osmotic press. tolerant plant by transformation of a plant by a recombinant vector contg. a gene (I) encoding choline oxidase. Also claimed are progeny having the same characteristics. XP–002084836.

SEQUENCE LISTING

```
<160> NUMBER OF SEQ ID NOS: 5

<210> SEQ ID NO 1
<211> LENGTH: 31
<212> TYPE: DNA
<213> ORGANISM: Wheat

<400> SEQUENCE: 1
ggaaggatcc tagaaattaa aacccagcgg c                              31

<210> SEQ ID NO 2
<211> LENGTH: 28
<212> TYPE: DNA
<213> ORGANISM: Wheat

<400> SEQUENCE: 2
ccgtcgacaa actctagctg atcaatcc                                  28
```

<210> SEQ ID NO 3
<211> LENGTH: 28
<212> TYPE: DNA
<213> ORGANISM: Wheat

<400> SEQUENCE: 3
ccgtcgacaa actgcagctg atcaatcc                                          28

<210> SEQ ID NO 4
<211> LENGTH: 224
<212> TYPE: PRT
<213> ORGANISM: Wheat

<400> SEQUENCE: 4

Met Gly Tyr Ser Lys Thr Leu Val Ala Gly Leu Phe Ala Met Leu Leu
 1               5                  10                  15

Leu Ala Pro Ala Val Leu Ala Thr Asp Pro Asp Pro Leu Gln Asp Phe
                20                  25                  30

Cys Val Ala Asp Leu Asp Gly Lys Ala Val Ser Val Asn Gly His Thr
            35                  40                  45

Cys Lys Pro Met Ser Glu Ala Gly Asp Asp Phe Leu Phe Ser Ser Lys
        50                  55                  60

Leu Ala Lys Ala Gly Asn Thr Ser Thr Pro Asn Gly Ser Ala Val Thr
 65                  70                  75                  80

Glu Leu Asp Val Ala Glu Trp Pro Gly Thr Asn Thr Leu Gly Val Ser
                 85                  90                  95

Met Asn Arg Val Asp Phe Ala Pro Gly Thr Asn Pro Pro His Ile
            100                 105                 110

His Pro Arg Ala Thr Glu Ile Gly Ile Val Met Lys Gly Glu Leu Leu
        115                 120                 125

Val Gly Ile Leu Gly Ser Leu Asp Ser Gly Asn Lys Leu Tyr Ser Arg
    130                 135                 140

Val Val Arg Ala Gly Glu Thr Phe Leu Ile Pro Arg Gly Leu Met His
145                 150                 155                 160

Phe Gln Phe Asn Val Gly Lys Thr Glu Ala Ser Met Val Val Ser Phe
                165                 170                 175

Asn Ser Gln Asn Pro Gly Ile Val Phe Val Pro Leu Thr Leu Phe Gly
            180                 185                 190

Ser Asn Pro Pro Ile Pro Thr Pro Val Leu Thr Lys Ala Leu Arg Val
        195                 200                 205

Glu Ala Arg Val Val Glu Leu Leu Lys Ser Lys Phe Ala Ala Gly Phe
    210                 215                 220

<210> SEQ ID NO 5
<211> LENGTH: 729
<212> TYPE: DNA
<213> ORGANISM: Wheat

<400> SEQUENCE: 5
ctgcagctga tcaatcctag ctaagcttat tacatagcaa gcatgggta ctccaaaacc       60 tagtagctg gcctgttcgc aatgctgtta ctagctccgg ccgtcttggc caccgaccca      120
gaccctctcc aggacttctg tgtcgccgac ctcgacggca aggcggtctc ggtgaacggg      180
cacacgtgca agcccatgtc ggaggccggc gacgacttcc tcttctcgtc caagttggcc     240
aaggccggca acacgtccac cccgaacggc tccgccgtga cggagctcga cgtggccgag     300
tggcccggta ccaacacgct gggtgtgtcc atgaaccgcg tggactttgc tcccggaggc     360

```
accaacccac cacacatcca cccgcgtgcc accgagatcg gcatcgtgat gaaaggtgag    420
cttctcgtgg gaatccttgg cagcctcgac tccgggaaca agctctactc gagggtggtg    480
cgcgccggag agacgttcct catcccacgg ggcctcatgc acttccagtt caacgtcggt    540
aagaccgagg cctccatggt cgtctccttc aacagccaga accccggcat tgtcttcgtg    600
cccctcacgc tcttcggctc caacccgccc atcccaacgc cggtgctcac caaggcactc    660
cgggtggagg ccagggtcgt ggaacttctc aagtccaagt ttgccgctgg gttttaattt    720
ctaggatcc                                                           729
```

PRODUCTION OF PATHOGEN RESISTANT PLANTS

CROSS REFERENCE PARAGRAPH

This application claims the benefit of U.S. Provisional Application No. 60/053,125, filed Jul. 18, 1997 and is herein incorporated by reference.

TECHNICAL FIELD

This invention relates to the genetic improvement of plants by the use of recombinant DNA techniques. Particularly, but not exclusively, the invention relates to the improvement of the tolerance of plants to pathogen attack.

BACKGROUND

Diseases of plants have caused an ongoing and constant problem in plant cultivation. The fungal pathogen, *Sclerotinia sclerotiorum*, in particular is said to cause disease in nearly 400 plant species. *Sclerotinia sclerotiorum* appears to be among the most nonspecific, omnivorous, and successful of plant pathogens. (Purdy, L. H., *Phytopathology* 69: 875–880 (1979))

Sclerotinia infections in sunflower, for example, are considered the major disease problems of the crop yet little genetic resistance is currently available to breeding programs to combat the various forms of this fungal infection. In fact, there are no major gene resistance mechanisms that have been defined in any species affected by this pathogen.

Oxalate (oxalic acid) is a diffusable toxin associated with various plant diseases, particularly those caused by fungi. While some leafy green vegetables, including spinach and rhubarb, produce oxalate as a nutritional stress factor, certain pathogens synthesize and export large amounts of oxalate to assist in the establishment and spread of the organism throughout infected hosts. Oxalate is used by pathogens to gain access into and subsequently throughout an infected plant. See for example, Mehta and Datta, *J. Biol. Chem.*, 266: 23548–23553, and published PCT application WO 92/14824 published in Sep. 3, 1992. Field crops such as sunflower, bean, canola, alfalfa, soybean, flax, safflower, peanut, clover, maize, sorghum, wheat, rice, as well as numerous vegetable crops, flowers, and trees are susceptible to oxalate-secreting pathogens. For example, fungal species including, but not limited to, Sclerotinia, Sclerotium, Aspergillus, Streptomyces, Penicillium, Pythium, Pacillus, Mycena, Leucostoma, Rhizoctonia and Schizophyllum use oxalic acid to provide an opportunistic route of entry into plants, causing serious damage to crops such as sunflower.

Enzymes that utilize oxalate as a substrate have been identified. These include oxalate oxidase (wheat oxalate oxidase is sometimes called germin) and oxalate decarboxylase. Oxalate oxidase catalyzes the conversion of oxalate to carbon dioxide and hydrogen peroxide. A gene encoding barley oxalate oxidase has been cloned from a barley root cDNA library and sequenced (See: PCT publication No. WO 92/14824, published in Sep. 3, 1992). A gene encoding wheat oxalate oxidase activity has been isolated and sequenced, and the gene has been introduced into a canola variety (PCT publication No. WO 92/15685 published in Sep. 17, 1992, Drawtewka-Kos, et al., *J. Biol. Chem.*, 264(9): 4896–4900 (1991)). Oxalate decarboxylase converts oxalate to carbon dioxide and formic acid. A gene encoding oxalate decarboxylase has been isolated from *Collybia velutipes* (now termed *Flammulina velutipes*) and the cDNA clone has been sequenced (WO 94/12622, published in Jun. 9, 1994). In addition, another oxalate decarboxylase gene has been isolated from *Aspergillus phoenices* (U.S. patent application Ser. No. 08/821,827, filed on Mar. 21, 1997).

Another gene which does not degrade oxalate, but which has been shown to help in the control of plant fungal pathogens is glucose oxidase. (See U.S. Pat. No. 5,516,671, filed on Nov. 3, 1994 and Wu, et al., *Plant Cell*, 7: 1357–1368 (1995)). In the presence of oxygen, glucose oxidase catalyzes the oxidation of glucose to σ-gluconolactone and hydrogen peroxide. It is thought that the hydrogen peroxide and the σ-gluconolactone, which is known as glycosyltransferase inhibitor, are responsible for the anti-pathogenic mode of action.

In many plants, attempted infection by avirulent pathogens triggers the activation of multiple defenses that may be accompanied by a hypersensitive response (HR) or collapse of host tissue around the site of pathogen penetration. A consequence of these responses is a restriction of pathogen spread within the host and frequently development of systemic acquired resistance (SAR) to subsequent infection by pathogens that may be taxonomically distant to the initial pathogen. For e.g., SAR induced by virus inoculation may be effective against subsequent attack by bacterial or fungal pathogens or vice versa. One of the earliest responses of the plant to infection is an oxidative burst which can be detected as an increased accumulation of superoxide ($O_2$) and/or hydrogen peroxide ($H_2O_2$). $O_2$ is very reactive and can form other reactive oxygen species, including hydroxyl radical (OH) and the more stable $H_2O_2$. $H_2O_2$ accumulation may trigger enhanced resistance responses in a number or ways: 1. Direct antimicrobial activity, 2. Act as a substrate for peroxidases associated with lignin polymerization and hence cell wall strengthening, 3. Via still to be determined mechanisms act as a signal for activation of expression of defense related genes, including those that result in stimulation of salicylic acid (SA) accumulation. SA is thought to act as an endogenous signal molecule that triggers expression of genes coding for several classes of pathogenesis-related proteins (PR proteins). Some of the PR proteins have antimicrobial enzymatic activities, such as glucanases and chitinases. The function of other PR proteins in defense still needs to be elucidated. Moreover, SA may potentiate the oxidative burst and thus act in a feedback loop enhancing its own synthesis. SA may also be involved in hypersensitive cell death by acting as an inhibitor of catalase, an enzyme that removes $H_2O_2$. 4. $H_2O_2$ may trigger production of additional defense compounds such as phytoalexins, antimicrobial low molecular weight compounds. For a review on the role of the oxidative burst and SA please see Lamb, C. and Dixon, R. A., *Ann. Rev. Physiol. Plant Mol. Biol.*, 48: 251–275 (1997). A high level of salicylic acid is associated with disease lesion mimic symptoms. Thus, the oxidative burst is the initial signal of a pathogen's attack, but one that is not permitted to be maintained by the plant. Even plants that are able to mount a defense are usually not immune to the disease. The pathogen is often able to inflict significant damage, although the plant may not die from the disease. Plants stressed because of pathogen damage are less likely to yield well and are often more susceptible to other types of pests.

In the present invention, it is demonstrated that the transgene encoding hydrogen peroxide/reactive oxygen species producing enzyme or an oxalate degrading enzyme is able to confer a significant pathogen resistance response in sunflower, canola, and soybean. Further, pathogen resistant sunflower expressing oxalate oxidase induces the expression of pathogenesis-related genes resulting in the accumulation of high levels of PR-1, chitinase and glucanase PR proteins as well as highly elevated levels of salicylic acid. Induction of the host defense systems has been shown in numerous cases to cause broad spectrum resistance to pathogens. For example, Chen, et al. in a 1993 Science article discusses that infection of plants by a pathogen often leads to enhanced resistance to subsequent attacks by the same or even unrelated pathogens (Chen, et al., *Science*, 262: 1883–1886 (1993)).

A lesion mimic-like phenotype also is observed in these SMF-3 transgenic plants. Sclerotinia resistant F1 hybrids of oxalate oxidase or oxalate decarboxylase transgenic plants crossed with existing Sclerotinia tolerant sunflower lines generated near-immune plants with no lesion mimic symptoms. A similar near-immune phenomenon is also observed with F1 hybrids of canola oxalate oxidase transgenics and an existing Sclerotinia tolerant line. Thus the synergistic effect of a hydrogen peroxide/reactive oxygen species producing enzyme or an oxalate degrading enzyme in a plant with a genetic pathogen tolerance gives rise to a near immune plant. A Sclerotinia immune plant has never been described before. It is now possible to take tolerant plants and make them immune or nearly immune to Sclerotinia. A pathogen immune plant can be expected to survive and yield well under pathogen challenge without the need for externally applied control agents such as chemical fungicides. Therefore, producers are spared the expense and effort required to treat fields for disease problems. In the case of Sclerotinia, for example, current treatment protocols are only partially effective and cost prohibitive. An effective transgenic approach to Sclerotinia disease control would therefore be of significant utility.

SUMMARY

The present invention relates to a method of producing resistance in plants to pathogens by the expression of a hydrogen peroxide/reactive oxygen species producing enzyme such as, but not limited to, oxalate oxidase (such enzyme(s) generally referred to herein as "reactive oxygen producing enzyme(s)") or a oxalate degrading enzyme such as, but not limited to oxalate decarboxylase in a conventionally tolerant background. The present invention also relates to a method of producing a Sclerotinia near-immune hybrid plant by crossing the appropriate transgenic plant expressing a hydrogen peroxide/reactive oxygen species producing enzyme or an oxalate degrading enzyme with pathogen tolerant lines or inbreds obtained through conventional genetic manipulations. Crossing the transgenic plant into a pathogen tolerant background produces a resistant plant with a high level of pathogen resistance, and no disease lesion mimic symptoms. The synergistic effect of expression of a hydrogen peroxide/reactive oxygen species producing enzyme or an oxalate degrading enzyme in a tolerant background gives significant and unexpectedly high resistance to the pathogen Sclerotinia.

Alternatively, the tolerant background plant could be used for transformation resulting in direct integration of a gene encoding the hydrogen peroxide/reactive oxygen species producing enzyme or oxalate degrading enzyme in a tolerant background.

Another embodiment of the invention relates to the overexpression of an endogenous plant gene. In some embodiments, isolated nucleic acids that serve as promoter or enhancer elements can be introduced in the appropriate position (generally upstream) of an endogenous form of the gene(s) encoding an enzyme of the present invention so as to up or down regulate expression of that enzyme.

Plants that could be transformed and made disease resistant include, but in no way are limited to; sunflower, bean, canola, alfalfa, soybean, flax, safflower, peanut, clover, maize, sorghum, wheat, rice, as well as numerous vegetable crops, flowers, and trees.

*rum* sclerotial body weight and number. Data is presented which separates the lines into appropriate comparisons; each of the non-transgenic parent lines, the non-transgenic hybrids (PK68F/SMF3, PK93M/SMF3, PR118M/SMF3 and PR126M/SMF3), transgenic SMF3 event 193870 (SMF3/35Soxox), and the transgenic hybrid with SMF3 event 193870 (PK68F/35Soxox, PK93M/35Soxox, PR118M/35Soxox, and PR126M/35Soxox). Numerical identification, listed under the bars in each graph, correspond to those presented in the table associated with Table 4. (abbreviations: wt.—weight, ct.—count, oxox=oxalate oxidase, 35S=35S promoter)

Figure 14:
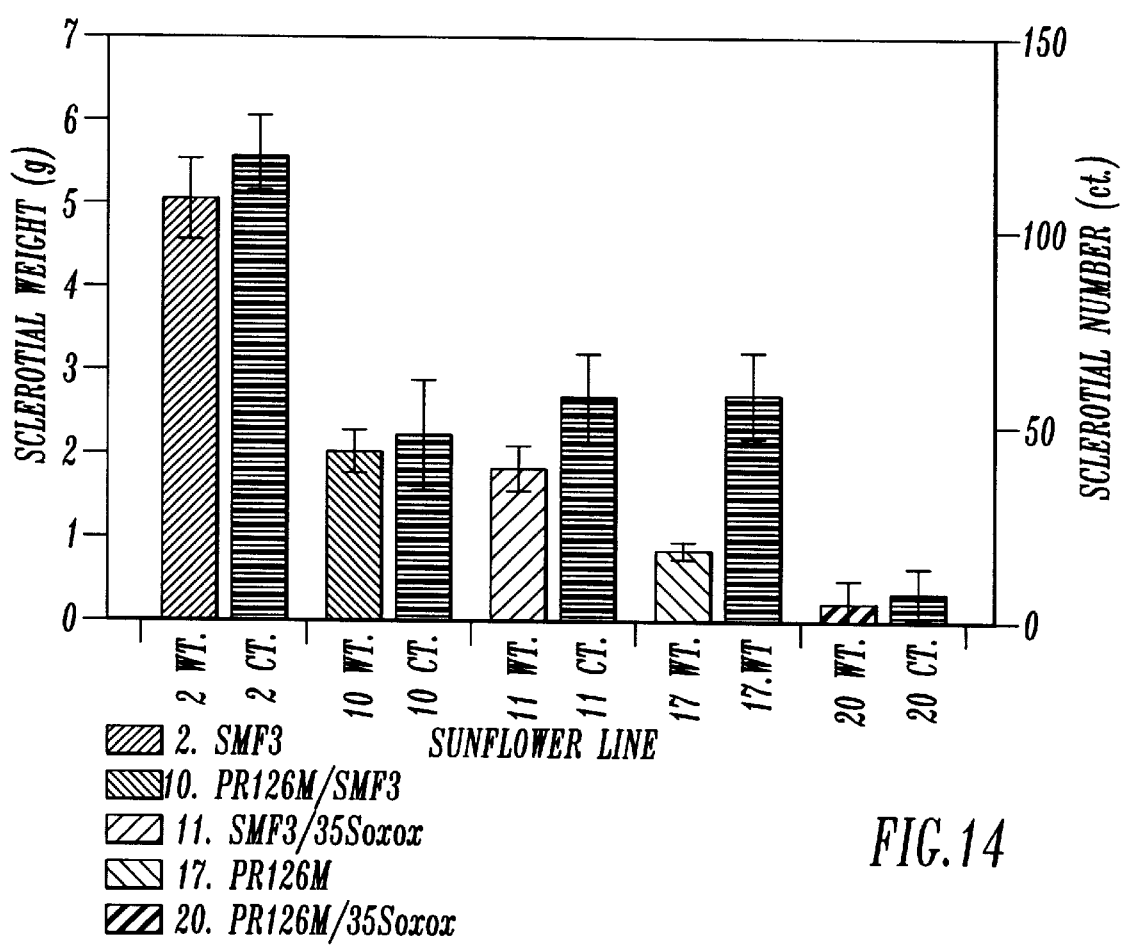

FIG. 14 shows the effect of sunflower line PR126M and the expression of oxalate oxidase on *Sclerotinia sclerotiorum* sclerotial body weight and number. Data is presented which separates the lines into appropriate comparisons; each of the non-transgenic parent lines, the non-transgenic hybrids (PK68F/SMF3, PK93M/SMF3, PR118M/SMF3 and PR126M/SMF3), transgenic SMF3 event 193870 (SMF3/35Soxox), and the transgenic hybrid with SMF3 event 193870 (PK68F/35Soxox, PK93M/35Soxox, PR118M/35Soxox, and PR126M/35Soxox). Numerical identification, listed under the bars in each graph, correspond to those presented in the table associated with Table 4. (abbreviations: wt.—weight, ct.—count, oxox=oxalate oxidase, 35S=35S promoter)

Figure 15:
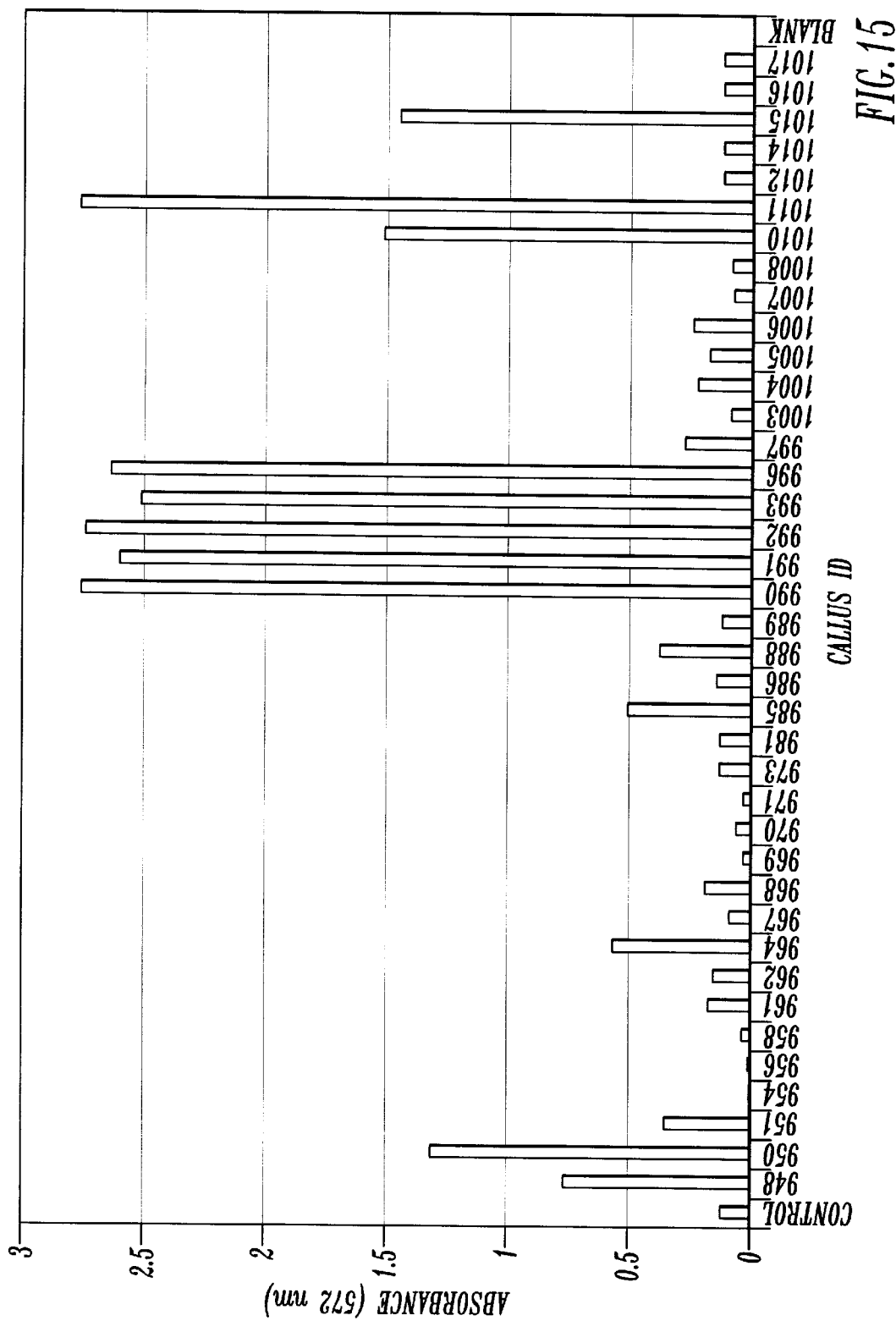

FIG. 15 shows the detection of galactose oxidase in maize callus.

DETAILED DESCRIPTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

In the description that follows, a number of terms are used extensively. The following definitions are provided to facilitate understanding of the invention.

A structural gene is a region of DNA having a sequence that is transcribed into messenger RNA (mRNA) that is then translated into a sequence of amino acids characteristic of a specific polypeptide. Structural genes also include gene encoding RNA products directly such as genes encoding transfer RNA (tRNA).

As used herein promoter includes reference to a region of DNA upstream from the start of transcription and involved in recognition and binding of RNA polymerase and other proteins to initiate transcription. A plant promoter is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples are promoters that preferentially initiate transcription in certain tissues, such as leaves, roots, seeds, fibres, xylem vessels, tracheids, or sclerenchyma. Such promoters are referred to, as tissue preferred. A cell type specific promoter primarily drives expression in certain cell types in one or more organs, for example, vascular cells in roots or leaves. An inducible promoter is a promoter that is under environmental control. Examples of environmental conditions that may effect transcription by inducible promoters include anaerobic conditions or the presence of light. Another type of promoter is a developmentally regulated promoter, for example a promoter that drives expression during pollen development. Tissue preferred, cell type specific, developmentally regulated, and inducible promoters constitute the class of non-constitutive promoters. A constitutive promoter is a promoter that is active under most environmental conditions.

An element is a region of DNA having a sequence that is involved in the regulation of gene expression. Examples of elements include terminators, introns, polyadenylation sequences, nucleic acid sequences encoding signal peptides which permit localization within a plant cell or secretion of the protein from the cell, or as in the present invention a nucleic acid sequence that regulates transcription in response to an inducer or the signal produced in response to an inducer.

An enhancer is a DNA regulatory region that can increase the efficiency of transcription, and may or may not be independent of the distance or orientation of the enhancer relative to the start site of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into protein.

A vector is a DNA molecule, such as a plasmid, cosmid, or bacteriophage, that has the capability of replicating autonomously in a host cell. Vectors typically contain one or a small number of restriction endonuclease recognition sites at which exogenous DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance, ampicillin resistance, or kanamycin resistance.

An expression vector is a DNA molecule comprising a gene that is expressed in a host cell. Typically, gene expression is placed under the control of certain regulatory regions, including constitutive or inducible promoters, tissue-specific regulatory regions, and enhancers. Such a gene is said to be operably linked to the regulatory regions.

An exogenous gene refers in the present description to a gene that is introduced into an organism either from a foreign species, or, if from the same species is substantially modified from its native form in composition and/or genomic locus by deliberate human invention. For example, any gene, even a structural gene normally found in the host plant, is considered to be an exogenous gene, if the gene is reintroduced into the organism.

An endogenous gene refers in the present description to a gene that is in its native form and has not been modified in composition or genomic locus.

A transgenic plant is a plant comprising a DNA region or modification to DNA introduced as a result of the process of transformation.

The term introduced in the context of inserting a nucleic acid into a cell, means transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

In eukaryotes, RNA polymerase II catalyzes the transcription of a structural gene to produce mRNA. A DNA molecule can be designed to contain a transcriptional template in which the RNA transcript has a sequence that is complementary to that of a specific mRNA.

Monocots are a large group of flowering plants, having an embryo with one cotyledon, parts of the flowers usually in threes, leaves with parallel veins and vascular bundles scattered throughout the stem. Examples of monocots include maize, barley, rice, sorghum and wheat.

Dicots are a large group of flowering plants, having an embryo with two cotelydons, parts of the flower usually in twos or fives or multiples, leaves with net veins, and vascular bundles in the stem in a ring surrounding the central pith. Examples of dicots are tobacco, petunia, canola, sunflower, soybean and tomato.

As used herein, the term plant includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

T0 refers to the initial transgenic shoot or plant recovered from the transformation and cultural protocols whether the plant is maintained in vitro or established in soil. The T1 generation are those plants resulting from seed recovered from, most commonly, self pollinated T0 plants, or from seed obtained by crosses with other lines where the T0 candidate is either the male or female parent. The T2 generation is the material obtained from T1 selfings or crosses.

The term oxidase as used in this application refers to an enzyme capable of generating hydrogen peroxide or any reactive oxygen species.

A pathogen refers to any organism responsible for disease and/or damage to a plant. For the present invention, pests include but are not limited to insects, fungi, bacteria, nematodes, viruses or viroids, parasitic weeds, and the like.

Stress refers to any force that can hurt or damage a plant. Examples of stress are pathogen attack, invasion by a parasitic weed, environmental stress such as heat, cold or drought, or mechanical damage. A stress resistant plant is one that is capable of surviving exposure to a stress. For example, a sunflower plant expressing oxalate oxidase is able to inhibit the establishment of pathogens, such as *Sclerotinia sclerotiorum*.

For the purposes of the present invention, a plant that is tolerant to a pathogen or other stress is one that is able to withstand a pathogen attack or stressful conditions better than the wild type plant, but will usually succumb to infection and/or die under conditions other than very light disease or stress pressure. A resistant plant is a plant having the ability to exclude or overcome the growth or effects of a pathogen or stress except under extremely high disease or stress pressure. An immune plant is one capable of complete disease resistance, with no reaction of plant tissue to a potential pathogen.

Plant genera

The hydrogen peroxide/reactive oxygen species producing enzymes in combination with a pathogen tolerant background, as described in the present invention can be used over a broad range of plant types, including species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Caco, and Populus.

Pathogens

As noted earlier, the hydrogen peroxide/reactive oxygen species producing enzymes of the invention can be utilized to protect plants from insect, disease, and parasitic weed pests. For purposes of the present invention, pests include but are not limited to insects, pathogens including fungi, bacteria, nematodes, viruses or viroids, parasitic weeds, and the like. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis,* European corn borer; *Agrotis ipsilon,* black cutworm; *Helicoverpa zea,* corn earworm; *Spodoptera frugiperda,* fall armyworm; *Diatraea grandiosella,* southwestern corn borer; *Elasmopalpus lignosellus,* lesser cornstalk borer; *Diatraea saccharalis,* sugarcane borer; *Diabrotica virgifera,* western corn rootworm; *Diabrotica longicornis barberi,* northern corn rootworm; *Diabrotica undecimpunctata howardi,* southern corn rootworm; Melanotus spp., wireworms; *Cyclocephala borealis,* northern masked chafer (white grub); *Cyclocephala immaculata,* southern masked chafer (white grub); *Popillia japonica,* Japanese beetle; *Chaetocnema pulicaria,* corn leaf beetle; *Sphenophorus maidis,* maize billbug; *Rhopalosiphum maidis,* corn leaf aphid; *Anuraphis maidiradicis,* corn root aphid; *Blissus leucopterus,* chinch bug; *Melanoplus femurrubrum,* redlegged grasshopper; *Melanoplus sanguinipes,* migratory grasshopper, *Hylemya platura,* seedcorn maggot; *Agromyza parvicornis,* corn bloth leafminer; *Anaphothrips obscurus,* grass thrips; *Solenopsis milesta,* thief ant; *Tetranychus urticae,* twospotted spider mite; Sorghum: *Chilo partellus,* sorghum borer; *Spodoptera frugiperda,* fall armyworm; *Helicoverpa zea,* corn earworm; *Elasmopalpus lignosellus,* lesser cornstalk borer; *Feltia subterranea,* granulate cutworm; *Phyllophaga crinita,* white grub; Eleodes, Conoderus, and Aeolus spp., wireworms; *Oulema melanopus,* cereal leaf beetle; *Chaetocnema pulicaria,* corn flea beetle; *Sphenophorus maidis,* maize billbug; *Rhopalosiphum maidis;* corn leaf aphid; *Sipha flava,* yellow sugarcane aphid; *Blissus leucopterus;* chinch bug; *Contarinia sorghicola,* sorghum midge; *Tetranychus cinnabarinus,* carmine spider mite; *Tetranychus urticae,* twospotted spider mite; Wheat: *Pseudaletia unipunctata,* army worm; *Spodoptera frugiperda,* fall armyworm; *Elasmopalpus lignosellus,* lesser cornstalk borer; *Agrotis orthogonia,* pale western cutworm; *Elasmopalpus lignosellus,* lesser cornstalk borer; *Oulema melanopus,* cereal leaf beetle; *Hypera punctata,* clover leaf weevil; *Diabrotica undecimpunctata howardi,* southern corn rootworm; Russian wheat aphid; *Schizaphis graminum,* greenbug; *Macrosiphum avenae,* English grain aphid; *Melanoplus femurrubrum,* redlegged grasshopper; *Melanoplus differentialis,* differential grasshopper; *Melanoplus sanguinipes,* migratory grasshopper; *Mayetiola destructor,* Hessian fly; *Sitodiplosis mosellana,* wheat midge; *Meromyza americana,* wheat stem maggot; *Hylemya coarctata,* wheat bulb fly; *Frankliniella fusca,* tobacco thrips; *Cephus cinctus,* wheat stem sawfly; *Aceria tulipae,* wheat curl mite; Sunflower: *Suleima helianthana,* sunflower bud moth; *Homoeosoma electellum,* sunflower moth; *Zygogramma exclamationis,* sunflower beetle; *Bothyrus gibbosus,* carrot beetle; *Neolasioptera murtfeldtiana,* sunflower seed midge; Cotton: *Heliothis virescens,* cotton boll worm; *Helicoverpa zea,* cotton bollworm; *Spodoptera exigua,* beet armyworm; *Pectinophora gossypiella,* pink bollworm; *Anthonomus grandis,* boll weevil; *Aphis gossypii,* cotton aphid; *Pseudatomoscelis seriatus,* cotton fleahopper; *Trialeurodes abutilonea,* bandedwinged whitefly; *Lygus lineolaris,* tarnished plant bug; *Melanoplus femurrubrum,* redlegged grasshopper; *Melanoplus differentialis,* differential grasshopper; *Thrips tabaci,* onion thrips; *Frankliniella fusca,* tobacco thrips; *Tetranychus urticae,* twospotted spider mite; Rice: *Diatraea saccharalis,* sugarcane borer; *Spodoptera frugiperda,* fall armyworm; *Helicoverpa zea,* corn earworm; *Colaspis brunnea,* grape colaspis; *Lissorhoptrus oryzophilus,* rice water weevil; *Sitophilus oryzae,* rice weevil; *Nephotettix nigropictus,* rice leafhopper; *Blissus leucopterus,* chinch bug; *Acrosternum hilare,* green stink bug; Soybean: *Pseudoplusia includens,* soybean looper; *Anticarsia gemmatalis,* velvetbean caterpillar; *Plathypena scabra,* green cloverworm; *Ostrinia nubilalis,* European corn borer; *Agrotis ipsilon,* black cutworm; *Spodoptera exigua,* beet armyworm; *Heliothis virescens,* cotton boll worm; *Helicoverpa zea,* cotton bollworm; *Epilachna varivestis,* Mexican bean beetle; *Myzus persicae,* green stink bug; *Melanoplus femurrubrum,* redlegged grasshopper; *Melanoplus differentialis,* differential grasshopper; *Hylemya platura,* seedcorn maggot; *Sericothrips variabilis,* soybean thrips; *Thrips tabaci,* onion thrips; *Tetranychus turkestani,* strawberry spider mite; *Tetranychus urticae,* twospotted spider mite; Barley: *Ostrinia nubilalis,* European corn borer; *Agrotis ipsilon,* black cutworm; *Schizaphis graminum,* greenbug; *Blissus leucopterus leucopterus,* chinch bug; *Acrosternum hilare,* green stink bug; *Euschistus servus,* brown stink bug; *Jylemya platura,* seedcorn maggot; *Mayetiola destructo,* Hessian fly; *Petrobia latens,* brown seedcorn maggot; *Mayetiola destructor,* Hessian fly; *Petrobia latens,* brown seedcorn maggot; *Mayetiola destructor,* Hessian fly; *Petrobia latens,* brown wheat mite; Oil Seed Rape: *Vrevicoryne brassicae,* cabbage aphid.

Generally Viruses include tobacco or cucumber mosaic virus, ringspot virus, necrosis virus, maize dwarf mosaic virus, etc. specific viral, fungal and bacterial pathogens for the major crops include: Soybeans: *Phytophthora megasperma* fsp. *Glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganensis* subsp. *Insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Rhizoctonia solani, Uromyces striatus, Colletotrichum trifolii* race 1 and race 2, *Leptosphaerulina briosiana, Stemphylium botryosum, Stagonospora meliloti, Sclerotinia trifoliorum,* Alfalfa Mosaic Virus, *Verticillium albo-atrum, Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Colletotrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herptotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomanes, Pythium graminicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahlia, Erwinia carotovora* pv. *carotovora, Cephalosporium acremonium, Phytophthora cryptogea, Albugo tragopogonis;* Maize: *Fusarium moniliforme* var. *subglutinans, Erwinia stewartii, Fusarium moniliforme, Gibberella zeae* (*Fusarium graminearum*), *Stenocarpella maydis* (*Diplodia maydis*), *Pythium irregulare, pythium debaryanum, Pythium graminicola, Pythium splendens, Pythium ultimum, Pythium aphanidermatum, Aspergillus flavus, Bipolaris maydis O, T Cochliobolus heterostrophus*), *Helminthosporium carbonum I, II & III* (*Cochliobolus carbonum*), *Exserohilum turcicum I, II & III, Helminthosporium pedicellatum, Physoderma maydis, Phyllosticta maydis, Kabatiella zea, Colletotrichum graminicola, Cercospora zeae-maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *Zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Spacelotheca reiliana, Physopella zeae, Cephalosporium maydis, Cephalosporium acremonium,* Maize chlorotic mottle virus, High plains virus, Maize mosaic virus, Maize rayado fino virus, Maize streak virus, Maize stripe virus, Maize rough dwarf virus; Sorghum: *Exserohilum turcicum, Colletotrichum graminicola* (*Glomerella graminicola*), *Cercospora sorghi, Gloeocercospora sorghi, Ascochyta sorghi, Pseudomonas syringae* p.v. *syringae, Xanthomonas campestris* p.v. *holcicola, Pseudomonas andropogonis, Puccinia purpurea, Macrophomina phaseolina, Periconia circinata, Fusarium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium relianum* (*Sphacelotheca reliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium Oxysporum, Pythium arrhenomanes, Pythium graminicola,* etc.

Generally parasitic weeds include the parasitic flowering plants Orobanche spp. (Broomrape), the mistletoes (Lorranthaceae: genera Arceuthobrium, Viscum, and Phoradendron, dodder (Cuscuta spp.), and Striga spp. (Witchweeds). Parasitic weeds of the present invention include, but are not limited to, Sunflower and Canola: *Orobanche aegyptiaca, Orabanche cumana,* Tomato and Potato: *Orobanche aegyptiaca, Orobanche ramosa, Orobanche cernua,* etc.

Hydrogen peroxide/reactive oxygen species producing enzymes

In the present invention, pathogen resistant plants are produced by introducing into the plant a gene, that codes for an enzyme, which causes the production of a reactive oxygen species by an interaction with an endogenously available substrate. Alternatively, the expression of an endogenous gene could be altered. Hydrogen peroxide or any reactive oxygen species may be produced. When hydrogen peroxide is produced degradation can result in production of reactive oxygen. However, hydrogen peroxide itself may be capable of inducing a stress response. Therefore, for purposes of this disclosure, the phrase "reactive oxygen species" is intended to include hydrogen peroxide. There are a number of enzymes that are capable of producing hydrogen peroxide or a reactive oxygen species, for example but not limited to, glucose oxidase, choline oxidase, galactose oxidase, L-aspartate oxidase, xanthine oxidase, monoamine oxidase, eosinophil peroxidase, glycolate oxidase, polyamine oxidase, copper amine oxidase, flavin amine oxidase, berberine Bridge Enzyme, choline oxidase, acyl coA oxidase, amino cyclopropane carboxylate oxidase (ACC oxidase), pyridoxamine-phosphate oxidase, sarcosine oxidase, sulfite oxidase, methyl sterol oxidase, aldehyde oxidase, xanthine oxidase, NADPH oxidase (respiratory burst enzyme homolog), large subunit (GP91) and most preferably, oxalate oxidase It is important in the present invention that the transgenic enzyme has available substrate in the plant. In the context of exogenous sunflower oxalate oxidase, there is endogenous oxalate present such that, upon expression of the gene, oxalate available to the enzyme is subject to degradation resulting in the formation hydrogen peroxide. The expression of genes induced by the unregulated presence of transgene-produced hydrogen peroxide/reactive oxygen species ultimately results in the accumulation of stress resistance related factors before such stresses are encountered. The hydrogen peroxide/reactive oxygen species is generated in such a manner that the disease or stress response mechanisms of the plant are activated. If a hydrogen peroxide or reactive oxygen species producing enzyme was selected that did not contain endogenous substrate, the plant could be transformed with a second gene which upon expression would result in substrate being made. Another option would be to transform plant A with the gene to a hydrogen peroxide or reactive oxygen species producing enzyme in a homozygous state, transform plant B with the gene to the substrate for the enzyme in a homozygous state, and then cross plant A with plant B. The resulting progeny would contain both the gene to the enzyme and the gene to the substrate.

Promoters

In order to express a hydrogen peroxide or reactive oxygen species producing gene, a promoter must be operably linked to that gene. Many different constitutive promoters can be utilized in the instant invention to express a hydrogen peroxide or reactive oxygen species producing gene. Examples include promoters from plant viruses such as the 35S promoter from cauliflower mosaic virus (CaMV), as described in Odell, et al., *Nature,* 313: 810–812 (1985), and hereby incorporated by reference, and promoters from genes such as rice actin (McElroy, et al., *Plant Cell,* 163–171 (1990)); ubiquitin (Christensen, et al., *Plant Mol. Biol.,* 12: 619–632 (1992); and Christensen, et al., *Plant Mol. Biol.,* 18: 675–689 (1992)); pEMU (Last, et al., *Theor. Appl. Genet.,* 81: 581–588 (1991)); MAS (Velten, et al., *EMBO J.,* 3: 2723–2730 (1984)); maize H3 histone (Lepetit, et al., *Mol. Gen. Genet.,* 231: 276–285 (1992); and Atanassvoa, et al., *Plant Journal,* 2(3): 291–300 (1992)), the 1'- or 2'-promoter derived from T-DNA of *Agrobacterium tumefaciens,* the Smas promoter, the cinnamyl alcohol dehydrogenase promoter (U.S. Pat. No. 5,683,439), the Nos promoter, the rubisco promoter, the GRP1–8 promoter, ALS promoter, as described in published PCT application WO 96/30530, a synthetic promoter, such as, Rsyn7, SCP and UCP promoters as described in U.S. patent application Ser. No. 09/028,819, filed Feb. 24, 1998 and herein incorporated by reference, and other transcription initiation regions from various plant genes known to those of skill.

In the present invention, an expression vector comprises a constitutive promoter operationally linked to a nucleotide sequence encoding for a hydrogen peroxide/reactive oxygen species producing gene. The expression vector and an accompanying, selectable marker gene under the direction of a plant-expressible constitutive promoter are introduced into plant cells, selective agent-resistant cells or tissues are recovered, resistant plants are regenerated and T0 candidates are screened for enzyme activity in leaf samples. T0 candidates can also be obtained without the use of a selectable marker. In this instance, the expression vector is introduced into plant cells without an accompanying selectable marker gene and transformed tissues are identified and plants screened based on enzyme activity alone.

Additional regulatory elements that may be connected to a hydrogen peroxide/reactive oxygen species producing or an oxalate degrading encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of the oxalate oxidase gene are known, and include, but are not limited to, 3' termination and/or polyadenylation regions such as those of the *Agrobacterium tumefaciens* nopaline synthase (nos) gene (Bevan, et al., *Nucl. Acids Res.*, 12: 369–385 (1983)); the potato proteinase inhibitor II (PINII) gene (Keil, et al., *Nucl. Acids Res.*, 14: 5641–5650 (1986) and hereby incorporated by reference); and An,, et al., *Plant Cell*, 1: 115–122 (1989)); and the CaMV 19S gene (Mogen, et al., *Plant Cell*, 2: 1261–1272 (1990)).

Plant signal sequences, including, but not limited to, signal-peptide encoding DNA/RNA sequences which target proteins to the extracellular matrix of the plant cell (Dratewka-Kos, et al., *J. Biol. Chem.*, 264: 4896–4900 (1989)) and the *Nicotiana plumbaginifolia* extension gene (DeLoose, et al., *Gene*, 99: 95–100 (1991)), or signal peptides which target proteins to the vacuole like the sweet potato sporamin gene (Matsuka, et al., *Proc. Nat'l Acad. Sci.* (USA), 88: 834 (1991)) and the barley lectin gene (Wilkins, et al., *Plant Cell*, 2: 301–313 (1990)), or signals which cause proteins to be secreted such as that of PRIb (Lind, et al., *Plant Mol. Biol.*, 18: 47–53 (1992)), or those which target proteins to the plastids such as that of rapeseed enoyl-Acp reductase (Verwaert, et al., *Plant Mol. Biol.*, 26: 189–202 (1994)) are useful in the invention. An especially useful signal sequence for this invention is signal sequence isolated from the oxalate oxidase gene. (Lane, et al., *J. Biol. Chem.*, 266(16): 10461–10469 (1991))

Gene Transformation Methods

Numerous methods for introducing foreign genes into plants are known and can be used to insert a gene into a plant host, including biological and physical plant transformation protocols. See, for example, Miki et al., (1993) "Procedure for Introducing Foreign DNA into Plants", In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al., *Science*, 227: 1229–31 (1985)), electroporation, micro-injection, and biolistic bombardment.

Expression cassettes and vectors and in vitro culture methods for plant cell or tissue transformation and regeneration of plants are known and available. See, for example, Gruber, et al., (1993) "Vectors for Plant Transformation" In: *Methods in Plant Molecular Biology and Biotechnology*, Glick and Thompson, eds. CRC Press, Inc., Boca Raton, pages 89–119.

Agrobacterium-mediated Transformation

The most widely utilized method for introducing an expression vector into plants is based on the natural transformation system of Agrobacterium. *A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, *Crit. Rev. Plant Sci.*, 10: 1–32 (1991). Descriptions of the Agrobacterium vector systems and methods for Agrobacterium-mediated gene transfer are provided in Gruber et al., supra; and Moloney, et al, *Plant Cell Reports*, 8: 238–242 (1989).

Direct Gene Transfer

Despite the fact that the host range for Agrobacterium-mediated transformation is broad, some major cereal crop species and gymnosperms have generally been recalcitrant to this mode of gene transfer, even though some success has recently been achieved in rice (Hiei et al., *The Plant Journal*, 6: 271–282 (1994)) and maize (Ishida, et al., *Nature Biotech.*, 14: 754–750 (1996)). Several methods of plant transformation, collectively referred to as direct gene transfer, have been developed as an alternative to Agrobacterium-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes. (Sanford, et al., *Part. Sci. Technol.*, 5: 27–37 (1987); Sanford, *Trends Biotech*, 6: 299–302 (1988); Sanford, *Physiol. Plant*, 79: 206–209 (1990); Klein, et al., *Biotechnology*, 10: 286–291 (1992)).

Another method for physical delivery of DNA to plants is sonication of target cells as described in Zang, et al., *BioTechnology*, 9: 996–996 (1991). Alternatively, liposome or spheroplast fusions have been used to introduce expression vectors into plants. See, for example, Deshayes, et al., *EMBO J.*, 4: 2731–2737 (1985); and Christou, et al., *Proc. Nat'l. Acad. Sci.* (USA), 84: 3962–3966 (1987). Direct uptake of DNA into protoplasts using $CaCl_2$ precipitation, polyvinyl alcohol or poly-L-ornithine have also been reported. See, for example, Hain, et al., *Mol. Gen. Genet.*, 199: 161 (1985); and Draper, et al., *Plant Cell Physiol.*, 23: 451–458 (1982).

Electroporation of protoplasts and whole cells and tissues has also been described. See, for example, Donn, et al., (1990) In: *Abstracts of the VIIth Int;l. Congress on Plant Cell and Tissue Culture IAPTC*, A2–38, page 53; D'Halluin et al., *Plant Cell*, 4: 1495–1505 (1992); and Spencer et al., *Plant Mol. Biol.*, 24: 51–61 (1994).

Particle Wounding/Agrobacterium Delivery

Another useful basic transformation protocol involves a combination of wounding by particle bombardment, followed by use of Agrobacterium for DNA delivery, as described by Bidney, et al., *Plant Mol. Biol.*, 18: 301–31 (1992). Useful plasmids for plant transformation include Bin 19. See Bevan, *Nucleic Acids Research*, 12: 8711–8721 (1984), and hereby incorporated by reference. This method is preferred for transformation of sunflower plants.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with Agrobacterium. To start the co-cultivation for intact meristems, Agrobacterium is placed on the meristem. After about a 3-day co-cultivation period the meristems are transferred to culture medium with cefotaxime plus kanamycin for the NPTII selection.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with Agrobacterium. For split meristems, after bombardment, the meristems are placed in an Agrobacterium suspension for 30 minutes. They are then removed from the suspension onto solid culture medium for three day co-cultivation. After this period, the meristems are transferred to fresh medium with cefotaxime plus kanamycin for selection.

Transfer by Plant Breeding

Alternatively, once a single transformed plant has been obtained by the foregoing recombinant DNA method, conventional plant breeding methods can be used to transfer the gene and associated regulatory sequences via crossing and backcrossing. Such intermediate methods will comprise the further steps of: (1) sexually crossing the disease-resistant plant with a plant from the disease susceptible taxon; (2) recovering reproductive material from the progeny of the cross; and (3) growing disease-resistant plants from the reproductive material. Where desirable or necessary, the agronomic characteristics of the susceptible taxon can be substantially preserved by expanding this method to include the further steps of repetitively: (1) backcrossing the disease-resistant progeny with disease-susceptible plants from the susceptible taxon; and (2) selecting for expression of a hydrogen peroxide producing enzyme activity (or an associated marker gene) among the progeny of the backcross, until the desired percentage of the characteristics of the susceptible taxon are present in the progeny along with the gene or genes imparting oxalic acid degrading and/or hydrogen peroxide enzyme activity.

By the term "taxon" herein is meant a unit of botanical classification. It thus includes, genus, species, cultivars, varieties, variants and other minor taxonomic groups which lack a consistent nomenclature.

Sclerotinia Disease

Sclerotinia overwinters as dense, black hyphal masses (sclerotia) deposited in the soil. Sclerotia in the soil germinate when favorable conditions are present to produce mycelial growth for root infections or apothecia for above ground ascospore production. Sclerotinia infection in sunflower manifests itself in 4 basic forms; basal root mycelial infection leading to wilt, and middle stalk, bud and head rots. Airborne ascospores from soil surface apothecia are responsible for the later three infections. The general view has been that Sclerotinia does not invade healthy tissue but gains a foothold only in wounded areas or senescing tissue where the spores happen to land. This does not appear to be strictly true, however, in that the only correlation to be made for successful ascospore infection in plants is the number of hours of continuous moisture to which spores are exposed during the germination process. Anywhere from 24 to 48 hours of damp conditions as well as some minimal level of plant exudate as a nutritional source are required for spore germination and penetration.

Fungal produced oxalate, in conjunction with a host of degradative enzymes, appears to be a requirement for infection (Noyes, R. D. and J. G. Hancock, *Physiol. Plant Pathol.,* 18(2): 123–132 (1981)). Mutant strains of Sclerotinia deficient in oxalate production are no longer pathogenic even though other degradative enzymes are produced (Godoy, G., et al., *Physiol. Mol. Plant. Pathol.,* 37(3): 179–191 (1990). In addition, oxalate fed to sunflower plants exhibit the wilt symptoms of Sclerotinia infection. Therefore, oxalate acts as a classic, diffusable toxin by stressing host plant tissue in preparation for enzymatic degradation and mycelial colonization (Maxwell, D. P., *Physiol. Plant Pathol.,* 3(2): 279–288 (1973)).

Tolerant backgrounds

The combination of a hydrogen peroxide producing enzyme or an oxalate degrading enzyme in a plant having a pathogen tolerant genetic background yields unexpectedly superior disease resistance compared to the expression of a hydrogen peroxide producing enzyme or an oxalate degrading enzyme in a non-tolerant background. Only in combination, does an immune or near immune plant result.

In the sunflowers expressing oxalate oxidase, oxalate oxidase-produced hydrogen peroxide induces the accumulation in the transgenics of factors associated with resistance to stress even though challenges such as pathogen attack are not present. Hydrogen peroxide acts as a signal to induce the expression of genes involved in stress resistance responses resulting in plants that stand ready for various challenges prior to encountering such conditions. Unfortunately, one of the side effects of a continuous, unregulated expression of resistance factors can be a lesion mimic phenotype. Lesion mimics are necrotic areas on leaves that resemble lesions that are present during pathogen assault. Lesion mimic phenotype, however, is not associated with pathogen infection but can be related to the inappropriate over-expression of genes leading to the accumulation of stress-related factors such as PR proteins, chitinase, glucanase and salicylic acid. Although not every genotype may produce a transgenic plant with the lesion mimic phenotype, in sunflower, the lesion mimic phenomenon associated with transgenic oxalate oxidase expression can be overcome by crossing the transgenic plant with other germplasm. In the present invention and in the context of *Sclerotinia sclerotiorum* resistance, oxalate oxidase expressing and lesion mimic exhibiting transgenics when crossed with several different sunflower inbreds no longer show lesion mimics while still exhibiting oxidase activity and varying levels of disease resistance. If such crosses are made to germplasm that already carries some tolerance to Sclerotinia, then not only is the lesion mimic response eliminated, but the resulting F1 plants are immune to the disease even though the hybrids are heterozygous for the transgene.

In sunflower, favored spore infection sites are the corollas in the head leading to fungal growth into the fleshy receptacle ultimately destroying the head, the depression at the nodal attachment point of petioles to the main stalk where water can accumulate, leaves and the young inflorescence. Root infections and wilt are more common in dry areas of sunflower production and can occur throughout the plant's life although infection from just before flowering to after flowering is most common. Middle stalk and head rots are found in more humid, damp areas and are commonly associated with flowering plants. Thus, tolerant varieties in sunflower can be tolerant in different parts of the plant. For example, but in no way limited to, the USDA has the following varieties of tolerant sunflower germplasm, HA410, HA411, HA412, and RHA801.

In canola, Sclerotinia disease is usually a problem only in the stem. In spring canola, Sclerotinia causes stem rot. In winter canola, stem rot and sometimes root rot can be found. In the canola quality germplasm, currently available, there is no significant stem rot tolerance. There is some tolerance in spring canola that originates from Europe (varieties Global, Hanna and Topas), but it is a weak tolerance and commercially unacceptable. In non-canola quality varieties, a stronger stem tolerance is present in Asiatic germplasm (Newman, et al., *Ann. Appl. Biol.* 110 (Supplement), 8: 150–157 (1987)). However, the stem tolerance is hard to detect, which makes the current tolerant varieties, using conventional methods, difficult to develop into canola quality material. Example 2, a partially tolerant canola quality line is crossed with a transgenic line containing the oxalate oxidase gene or the oxalate decarboxylase gene. For the first time, an enhanced level of tolerance was seen in the resulting progeny over what can be obtained through conventional breeding.

In other plants, different levels and types of tolerance can be found. For example, Pioneer has two soybean varieties that are tolerant to Sclerotinia. Thus, for the present invention, it would be possible to use different tolerant germplasm as the source to cross with transgenic plants expressing a hydrogen peroxide/reactive oxygen species producing enzyme or an oxalate degrading enzyme or to introduce the enzyme into the tolerant plant or tissue or to over express an endogenous enzyme. The resulting progeny may have various levels of resistance to the pathogen, because of differing tolerant genetic backgrounds, but a synergistic effect is still seen when a tolerant background is combined with the expression of a hydrogen peroxide/reactive oxygen species producing gene or an oxalate degrading enzyme.

In maize, several varieties of maize tolerant to *Aspergillus flavus* and the species of Penicillium responsible for ear mold are possible pathogens that can be used in the present invention. Again, for the present invention, it would be possible to use different tolerant germplasm as the source to cross with transgenic plants expressing a hydrogen peroxide/reactive oxygen species producing enzyme or an oxalate degrading enzyme or to introduce the enzyme into the tolerant plant or tissue or to over express an endogenous enzyme. The resulting progeny may have various levels of resistance to the pathogen, because of differing tolerant genetic backgrounds, but a synergistic effect is still seen when a tolerant background is combined with the expression of a hydrogen peroxide/reactive oxygen species producing gene or an oxalate degrading enzyme. Examples of Aspergillus tolerant maize varieties are the Tex6, Y7, Mp420, LB31, L317, C12, N6, 75-R001, B37Ht-2, OH513, and H103 (see Campbell, et al., *Plant Disease* 79(10):139–1045 (1995) and Campbell, et al., *Phytopathology* 85(8):886–896 (1995)).

Introduction of a hydrogen peroxide/reactive oxygen species generating enzyme or oxalate degrading enzyme into a tolerant background As described earlier and in the following Example sections, one way of introducing a hydrogen peroxide/reactive oxygen species producing enzyme or oxalate degrading enzyme is by transforming a non-tolerant plant with an expression vector containing the enzyme and regenerating plants. Next the transgenic plants expressing the enzyme are crossed with a plant tolerant to the pathogen.

Alternatively, a tolerant plant or plant tissue could be transformed with the expression vector containing the enzyme. The resulting plant would contain both a transgene expressing the enzyme and a genetically tolerant background.

Another method could be overexpression of an endogenous gene. In some embodiments, isolated nucleic acids that serve as promoter or enhancer elements can be introduced in the appropriate position (generally upstream) of an endogenous form of the gene(s) encoding an enzyme of the present invention so as to up or down regulate expression of that enzyme. For example, endogenous promoters can be altered in vivo by mutation, deletion, and/or substitution (see: Kmiec, U.S. Pat. No. 5,565,350; Zarling et al., PCT/US93/03868), or isolated promoters can be introduced into a plant cell in the proper orientation and distance from a hydrogen peroxide/reactive oxygen species producing gene so as to control the expression of the gene. Gene expression can be modulated under conditions suitable for plant growth so as to alter the enzyme content and/or composition. Thus, the present invention provides compositions, and methods for making, exogenous promoters and/or enhancers operably linked to a native, endogenous form of an enzyme of the present invention.

There are a number of endogenous genes that generated hydrogen peroxide/reactive oxygen species. The following is a list of possible enzymes whose expression could be altered by the method described earlier. Oxidoreductases that would be expected to produce reactive oxygen intermediates such as hydrogen peroxide: Hydrogen peroxide-forming: oxalate oxidase EC 1.2.3.4, glycolate oxidase EC 1.1.3.15, polyamine oxidase EC 1.5.3.11, copper amine oxidase EC 1.4.3.6, flavin amine oxidase EC 1.4.3.4, berberine Bridge Enzyme EC 1.5.3.9, choline oxidase EC 1.1.3.7, acyl coA oxidase EC 1.3.3.6, amino cyclopropane carboxylate oxidase (ACC oxidase), pyridoxamine-phosphate oxidase EC 1.4.3.5, sarcosine oxidase EC 1.5.3.1, sulfite oxidase EC 1.8.3.1, and methyl sterol oxidase, Superoxide-forming: aldehyde oxidase EC 1.2.3.1, xanthine Oxidase EC 1.1.3.22, and NADPH Oxidase (respiratory burst enzyme homolog), large subunit (GP91).

Example 1

Sunflower

Cloning of wheat oxalate oxidase

Pioneer wheat variety 2548 (PVP#8900112) was imbibed with running water for one hour, wrapped in moist paper towels, sealed in zip-lock plastic bags, and incubated in the dark at 28° C. for 24 hours. Germinating seed was then frozen in liquid nitrogen and aliquots of 5 to 10 grams were stored at −80° C.

A modified protocol for Castor endosperm RNA isolation was used for RNA purification. (Prescott and Martin, *Plant Molec. Bio. Rep.*, 4(#4): 219–224 (1987)) Six grams of frozen germinating seed was ground in liquid nitrogen using a mortar and pestle. Fifty milliliters of extraction buffer (150 mM LiCl, 50 mM Tris pH 8.0, 5 mM EDTA, 5% (w/v) sodium dodecyl sulfate) was added to the powdered wheat and mixed with 50 mls of Phenol/chloroform/isoamyl-alcohol (25:24:1). This was mixed in a Waring blender for one minute. The homogenate was added to 50 ml conical centrifuge tubes and centrifuged in a Juoan 412 centrifuge at 3000 rpm for 10 minutes. The aqueous phase was then extracted two more times with an equal volume of phenol/chloroform/isoamyl-alcohol and finally with an equal volume of chloroform. The aqueous phase was then removed to a baked Corex centrifuge tube and one fourth volume of 10M LiCl added (final concentration approximately 2M LiCl). This was placed at −20° C. overnight. The RNA was collected by centrifugation at 10K for 60 minutes and removing all of the supernatant by aspiration with sterile pipettes. The RNA pellet was resuspended in sterile water and quantitated by spectroscopy at OD 260. Gibco/BRL's Superscript First Strand Synthesis Kit was used to make first strand cDNA from the total RNA. The synthesis was primed using oligo dT. All other steps were as stated in the suppliers protocol. PCR was carried out on the first strand cDNA using oligos DO4244 and DO4245.

DO4244 is 5'>ggaaggatcctagaaattaaaacccagcggc>3' (SEQ ID NO: 1)

DO4245 is 5'>ccgtcgacaaactctagctgatcaatcc>3' (SEQ ID NO: 2)

50 µl reaction:

1 µl first strand cDNA

5 µl 10× buffer

1 µl 25 mM dNTPs

1 μl oligo 4244 (1 μg/μl)
1 μl oligo 4245 (1 μg/μl)
1 μl TAQ polymerase
40 μl water A MJResearch PTC100 thermocycler program was used as follows:
1: 92° C. 1 min.
2: 92° C. 30 sec.
3: 55° C. 30 sec.
4: 72° C. 2 min.
5: Go to step 2 29 times.
6: 72° C. 5 min.
7: 4° C. for ever
8: END The PCR band that resulted was isolated by gel electrophoresis and purified by phenol extraction of the DNA from the agarose. This was digested with BamHI and SalI for cloning into pGem3ZF+ (Promega, Madison, Wis.) also cut with BamHI and SalI.. Ligation of these two DNA's did not yield the expected plasmid. A new primer was designed for the 5' end, DO5597, 5'>ccgtcgacaaactgcagctgatcaatcc>3' (SEQ ID NO: 3).

50 μl reaction:
1 μl first PCR band
5 μl 10× buffer
1 μl 25 mM dNTPs
1 μl oligo 4244 (1 μg/μl)
1 μl oligo 5597 (1 μg/μl)
1 μl TAO polymerase
40 μl water A MJResearch PTC100 thermocycler program was used as follows:
1: 92° C. 30 sec.
2: 65° C. 30 sec.
3: Go to 1.29 times
4: 75° C. 5 min.
5: END The PCR band that resulted was isolated by gel electrophoresis and purified by phenol extraction of the DNA from the agarose. This was digested with BamHI and PstI for cloning into pGem3ZF+ also cut with BamHI and PstI. Ligation of these two DNA's did yield the expected plasmid, with one unexpected change. The small polylinker region of pGem3ZF+ between the BamHI and PstI sites was duplicated on each end of the oxalate oxidase cDNA. This resulted in reversing the insert in the parental backbone. This DNA was sent to Iowa State University's Nucleic Acid Facility for sequence verification. The only differences are the restriction sites added to the ends by PCR for cloning. The oxalate oxidase protein precursor sequence is illustrated by SEQ ID NO: 4. The oxalate oxidase cDNA sequence is illustrated in SEQ ID NO: 5.

The plasmids used in this application are pPHP7746 and pPHP8188. Plasmid pPHP7746 contains a pBin19 backbone with two plant transcription units between TDNA borders. The plant transcription units are 1xCaMV35S promoter-::omega prime leader::oxalate oxidase::pinII terminator and a selectable marker. Plasmid pPHP8188 also contains a pBin19 backbone with two plant transcription units between TDNA borders. The plant transcription units are Brassica ALS promoter::oxalate oxidase::pinII terminator and a selectable marker.

Sunflower Transformation

A general method for transformation of sunflower meristem tissues is practiced as follows (see also European patent number 486233, herein incorporated by reference, and Malone-Schoneberg, J., et al., *Plant Science,* 103: 199–207 (1994)).

Mature sunflower seed (*Helianthus annuus* L.) of Pioneer® hybrid 6440 or research selection SMF-3 (a selection of USDA germplasm release SFM-3; cms/*H. petiolaris* Nuttall//cms HA89 backcross) were dehulled using a single wheat-head thresher. The seed was provided by the Pioneer sunflower research station at Woodland, Calif. Seeds were surface sterilized for 30 minutes in a 20% Chlorox bleach solution with the addition of two drops of Tween 20 per 50 ml of solution. The seeds were rinsed twice with sterile distilled water.

Split embryonic axis explants were prepared by a modification of procedures described by Schrammeijer et al. (Schrammeijer, et al., *Plant Cell Rep.,* 9: 55–60 (1990)). Seeds were imbibed in distilled water for 60 minutes following the surface sterilization procedure. The cotyledons of each seed were then broken off producing a clean fracture at the plane of the embryonic axis. Following excision of the root tip, the explants were bisected longitudinally between the primordial leaves. The two halves were placed, cut surface up, on GBA medium consisting of Murashige and Skoog mineral elements (Murashige, et al., *Physiol. Plant,* 15: 473–497 (1962)), Shepard's vitamin additions (Shepard, (1980) In: *Emergent Techniques for the Genetic Improvement of Crops,* University of Minnesota Press), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6 and 8 g/l Phytagar.

The explants were subjected to microprojectile bombardment prior to Agrobacterium treatment (Bidney, et al., *Plant Mol. Biol.,* 18: 301–313 (1992)). Thirty to forty explants were placed in a circle at the center of a 60×20 mm plate for this treatment. Approximately 4.7 mg of 1.8 mm tungsten microprojectiles were re-suspended in 25 ml of sterile TE buffer (10 mM Tris HCl, 1 mM EDTA, pH 8) and 1.5 ml aliquots were used per bombardment. Each plate was bombarded twice through a 150 mm nytex screen placed 2 cm above the samples in a PDS 1000® particle acceleration device.

Disarmed *Agrobacterium tumefaciens* strain EHA105 were used in all transformation experiments. Binary vectors were introduced into EHA105 using a freeze-thaw transformation method (Holsters, et al., *Mol. Gen. Genet.,* 163: 181–187 (1978)). Bacteria for plant transformation experiments were grown overnight (28° C. and 100 RPM continuous agitation) in liquid YEP medium (10 gm/l yeast extract, 10 gm/l Bactopeptone and 5 gm/l NaCl, pH 7.0) with the appropriate antibiotics required for bacterial strain and binary plasmid maintenance. The suspension was used when it reached an $OD_{600}$ of about 0.4 to 0.8. The Agrobacterium cells were pelleted and re-suspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants were placed in an Agrobacterium suspension, mixed and left undisturbed for 30 minutes. The explants were then transferred to GBA medium and co-cultivated cut surface down at 26° C. and 18 hour days. After three days of co-cultivation, the explants were transferred to 374B: (GBA medium lacking growth regulators and a reduced sucrose level of 1%) supplemented with 250 mg/l cefotaxime and 50 mg/l kanamycin sulfate. The explants were cultured for 2 to 5 weeks on selection and then transferred to fresh 374B medium lacking kanamycin for 1 to 2 weeks of continued development. Explants with differentiating, antibiotic resistant areas of growth that had not produced shoots suitable for excision were transferred to GBA medium containing 250 mg/l cefotaxime for a second 3 day phytohormone treatment. Leaf samples from green, kanamycin resistant shoots were assayed for the presence of NPTII by ELISA and for the presence of oxalate degrading transgene expression by oxalate oxidase or oxalate decarboxylase enzyme assays.

NPTII positive shoots were grafted to Pioneer® hybrid 6440 in vitro grown sunflower seedling rootstock. Surface sterilized seeds were germinated in 48-0 medium (half strength Murashige and Skoog salts, 0.5% sucrose, 0.3% gelrite, pH 5.6) and grown under conditions described for explant culture. The upper portion of the seedling was removed, a 1 cm vertical slice was made in the hypocotyl and the transformed shoot inserted into the cut. The entire area was wrapped with parafilm to secure the shoot. Grafted plants could be transferred to soil following 1 week of in vitro culture. Grafts in soil were maintained under high humidity conditions followed by a slow acclimatization to the greenhouse environment. Transformed sectors of $T_0$ plants (parental generation) maturing in the greenhouse were identified by NPTII ELISA and/or by oxalate oxidase or oxalate decarboxylase activity analysis of leaf extracts while transgenic seeds harvested from N PTII positive $T_0$ plants were identified by oxalate oxidase or oxalate decarboxylase activity analysis of small portions of dry seed cotyledon.

An alternative sunflower transformation protocol allows the recovery of transgenic progeny without the use of chemical selection pressure. Seeds were dehulled and surface-sterlized for 20 min in a 20 percent Chlorox bleach solution with the addition of two to three drops of Tween 20 per 100 ml of solution, then they were rinsed three times with distilled water. Sterilized seeds were imbibed in the dark at 26° C. for 20 h on filter paper moistened with water. The cotyledons and root radical were removed, and the meristem explants were cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 h under the dark. The primary leaves were removed to expose the apical meristem, around 40 explants were placed with the apical dome facing upward in a 2 cm circle in the center of 374M (GBA medium with 1.2% Phytagar) and then cultured on the medium for 24 h in the dark.

Approximately 18.8 mg of 1.8 $\mu$m tungsten particles were resuspended in 150 $\mu$l absolute ethanol. After sonication, 8 $\mu$l of it was dropped on the center of the surface of macrocarrier. Each plate was bombarded twice with 650 psi rupture discs in the first shelf at 26 mm of Hg helium gun vacuum.

The plasmid of interest was introduced into Agrobacterium tumefaciens stain EHA 105 via freeze thawing as described by Holsters et al., *Mol. Gen. Genet.* 163: 181–7 (1978). The pellet of overnight grown Agrobacteria at 28° C. in a liquid YEP medium (10 g/l yeast extract, 10 g/l Bacto peptone and 5 g/l NaCl, pH 7.0) in the presence of 50 $\mu$g/l kanamycin was resuspended in an inoculation medium (12.5 mM 2-mM 2-(N-morpholino) ethanesulfonic acid, MES, 1 g/l NH4Cl and 0.3 g/l MgSO4 at pH 5.7) to reach an final concentration of 4.0 at OD 600. Particle-bombarded explants were transferred to GBA medium (374E), a droplet of bacteria suspension was placed directly onto the top of meristem. The explants were co-cultivated on the medium for 4 days after which the explants were transferred to 374 C medium (GBA with 1% sucrose and no BAP, IAA, GA3 and supplemented with 250 $\mu$g/ml cefotaxime). The plantlets were cultured on the medium for about 2 weeks under 16 h day and 26° C. incubation conditions.

Explants (around 2 cm long) from two week culture in 374C medium were screened by oxalate oxidase or oxalate decarboxylase assays. After oxalate oxidase or decarboxylase positive explants were identified, those shoots that failed to exhibit oxalate oxidase activity were discarded, and every positive explant was subdivided into nodal explants. One nodal explant contained at least one potential node. The nodal segments were cultured on GBA medium for three to four days to promote the formation of auxiliary buds from each node. Then they were transferred to 374C medium and allowed to develop for additional four weeks. Developing buds were separated and cultured for an additional four weeks on 374C medium. Pooled leaf samples from each newly recovered shoot were screened again by the appropriate enzyme assay. At this time, the enzyme positive shoots recovered from a single node will generally have been enriched in the transgenic sector detected in the initial assay prior to nodal culture.

Recovered oxidase or decarboxylase positive shoots were grafted to Pioneer hybrid 6440 in vitro grown sunflower seedling rootstock. The rootstocks were prepared in the following manner. Seeds were dehulled and surface-sterilized for 20 min in a 20 percent Chlorox bleach solution with the addition of two to three drop of Tween 20 per 100 ml of solution, and were rinsed three times with distilled water. The sterilized seeds were germinated on the filter moistened with water for three days, then they were transferred into 48 medium (half strength MS salt, 0.5% sucrose, 0.3% gelrite pH 5.0) and grown at 26° C. under the dark for 3 days, then incubated at 16 h day culture condition. The upper portion of selected seedling was removed, a vertical slice was made in each hypocotyl, and a transformed shoot was inserted into a V-cut. The cut area was wrapped with parafilm. After one week culture on the medium, grafted plants were transferred to soil. In the first two weeks, they were maintained under high humidity conditions to acclimatize a greenhouse environment.

Transformed sectors of To plants were identified by additional oxalate oxidase or decarboxylase assays of those in vitro positive grafted shoots. After assay, non-transformed sectors were trimmed off and auxiliary buds from transgenic sectors were recovered so as to obtain near uniform transformation events. Selfed seed from TO's were collected, germinated, characterized for enzyme activity, and selfed again.

Oxalate Oxidase Expression in Sunflower Transgenics

A small set of wheat oxalate oxidase expressing sunflower transgenics were forwarded to the Pioneer sunflower breeding station at Woodland, Calif. for Sclerotinia disease resistance evaluation. A mycelial inoculation protocol was developed where the pathogen was introduced to the plant through small pieces of Sclerotinia infested carrot. A freshly infected carrot slice was placed on a petiole midway between the stem and leaf. A parafilm wrap was applied to hold the carrot piece in place and to maintain a high humidity environment at this junction. Three middle level petioles/plant were inoculated on greenhouse grown plants prior to first ring anthesis. The carrot piece was removed 24 hours later and disease progression was monitored as the fungus moved into the stem. Approximately 3 weeks later a visual rating was taken of the lesions on the stem and given a value of 1 to 9 where 1 represented typical susceptible lesions and 9 denoted a high degree of resistance. The same readings were done 7–8 days later. In addition, the inoculated plants were collected at dry down, the main stems split and the fungal sclerotia bodies were recovered, weighed and counted.

The initial set of 5 oxalate oxidase expressing T2 transgenics (line SMF-3) recovered from pPHP7746 transformations showed remarkable disease resistance responses following fungal challenge. While adequate quantitative data to correlate oxidase activity with resistance ratings were not collected with this first set of plants, it was visually apparent that the transgenics were significantly more resistant to Sclerotinia mycelial infection than the nontransgenic controls (nontransformed SMF-3). Disease would easily progress down the petiole of all inoculated plants, however, in a number of the transgenics further progression into the stem was either restricted or halted at the stem. There were indications that the higher expressing oxidase transgenics inhibited disease progression to a greater extent than lower expressing individuals. In the end, all nontransgenic plants were dead while many of the transgenics were able to survive to produce seed. Although the plants showed significant disease resistance, the plants themselves had numerous disease-like lesions on their leaves. This phenomena is often seen in mutants that have a non-functional or modified gene in the disease resistance pathway. Although the overall health and seed yield of the sunflower plants did not seem to be strongly affected under greenhouse conditions, plant with lesions would not be commercially viable and may not maintain their yield in field conditions.

Infection experiments with this initial set of transgenics have been designed to determine the correlation between transgene activity and disease resistance response. The results are with a set of T2 plants of the best performing event in the initial trial, #193870. Data from 19 transgenic plants and 23 controls were collected following fungal inoculation. On the day of inoculation, the leaf and part of the petiole above the inoculation site of each treated petiole were removed, and shipped to Johnston, overnight express, on wet ice. The samples were lyophilized to dryness and equal portions of petiole or leaf associated with each of the 3 inoculated petioles were pooled and ground to a fine powder. Oxidase enzyme assays (Suigura, et al., *Chem. Pharm. Bull.*, 27(9): 2003–2007 (1979) and hereby incorporated by reference) were performed on each leaf and petiole sample. The oxidase enzyme assays are as follows: (1) Leaf tissue was lyophilized and grind to a fine powder. The powder was resuspended in Na-succinate buffer (0.1M, pH 3.5)+a drop of Tween-20 at a 1 mg/ml concentration; (2) Individual 1 ml reactions were set up in tubes or a larger volume reaction mix in a small beaker with stirring for a time course. Into each tube: Tube assay—100 µl of suspension, 100 µl of 10 mM oxalate in 0.1M Na-succinate buffer, pH 3.5, succinate buffer to bring volume to 1 ml. Tissue extract was added last and this started the reaction timing. The reaction was allowed to proceed for a defined time (1–30 minutes) with agitation and 100 µl of reaction mix was removed to microtitre plate wells that contain 17.5 µl of 1M Tris free base. Then 82.5 µl was added of the peroxidase-linked color development solution (8 mg 4-aminoantipyrine, 20 µl N,N-dimethylaniline, 400 ul of peroxidase all in 100 ml of 0.2M Tris-HCl, pH 7.0). The absorbance was read at 550 nm. For the time course assay, successive 100 ul aliquots were removed from the 1 ml reaction tube at the desired times. Time vs. absorbance was plotted and a slope was determined (OD550/min.). This value based on the initial dry weights can be used to compare different samples and plants.

The enzyme assay results are presented as either a slope of a time course reaction, A550/minute, or as a "specific activity" calculated from a slope (mM oxalate converted/minute/mg powder). A summary table is as follows:

TABLE 1

|  | # | Avg. oxidase activity (mM oxalate/min/mg) petiole | leaf | (1 = sus., 10 = res.) Lesion-1 | Lesion-2 | Sclerotia wt. (gm) | Sclerotia # |
|---|---|---|---|---|---|---|---|
| Controls | 23 | 0 | 0 | 2.2 | 1.1 | 4.0 | 84 |
| 193870 | 19 | 71.6 | 119 | 7.6 | 6.1 | 0.43 | 11.4 |

The transgenics exhibited not only a significant improvement in the subjective disease ratings compared to the nontransgenic controls, but also showed a 10 fold decrease in the amount of fungal formed sclerotia deposited in the stems. 35S oxalate oxidase expression effectively disrupts a middle stalk rot-type of mycelial Sclerotinia invasion by dramatically reducing the rate of movement of the disease front through tissue as well as impacting the ability of the fungus to produce storage bodies that would serve as inoculum in subsequent crop cycles.

In addition to the observations with the 193870 T2 transgenic four trials of a small set of 35S::oxalate oxidase transgenics transformed with pPHP7746 were performed.

Figure 1:
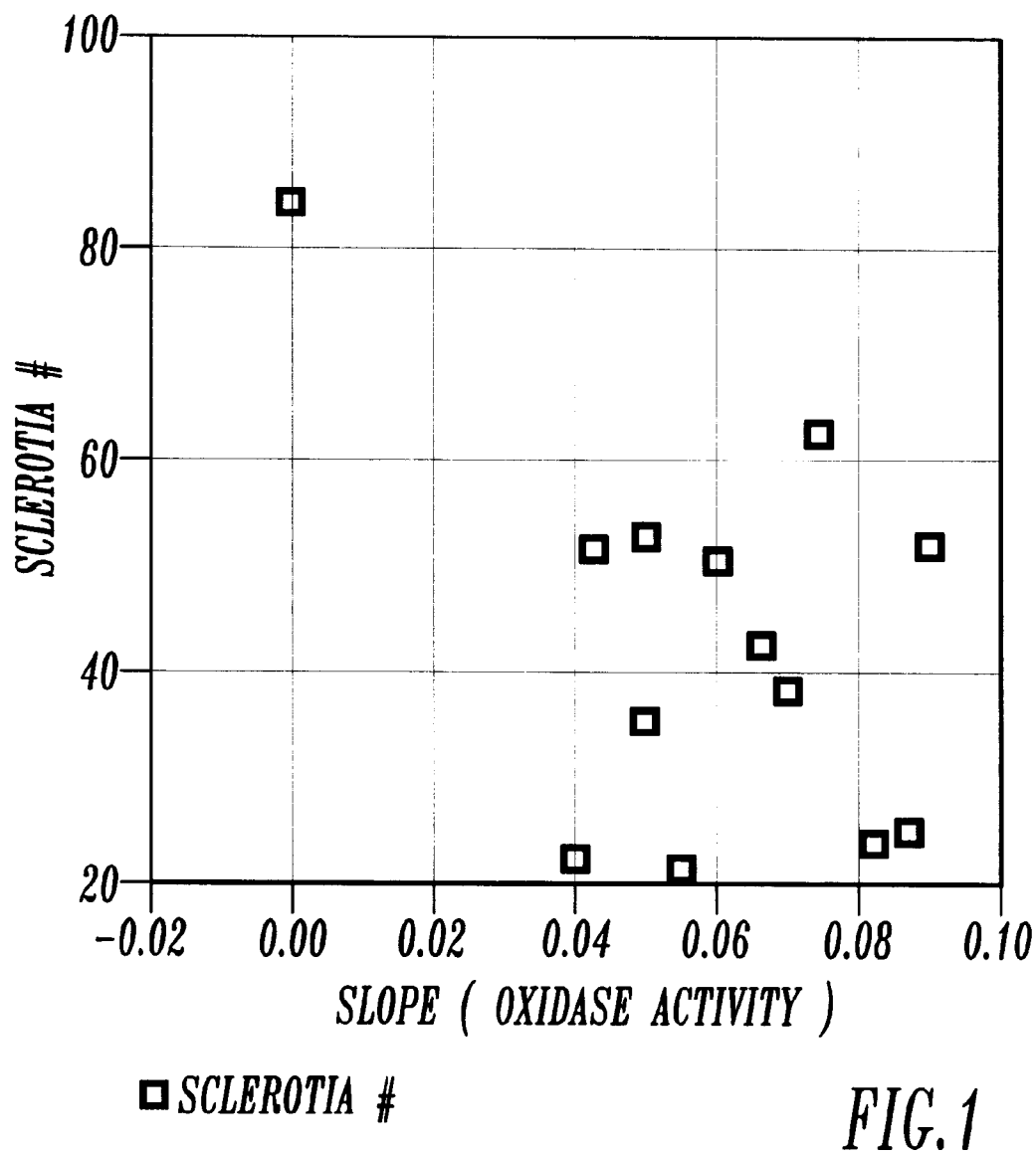
FIG. 1 shows the slope of the oxalate oxidase activity versus the number of sclerotia in sunflower.
Figure 2:
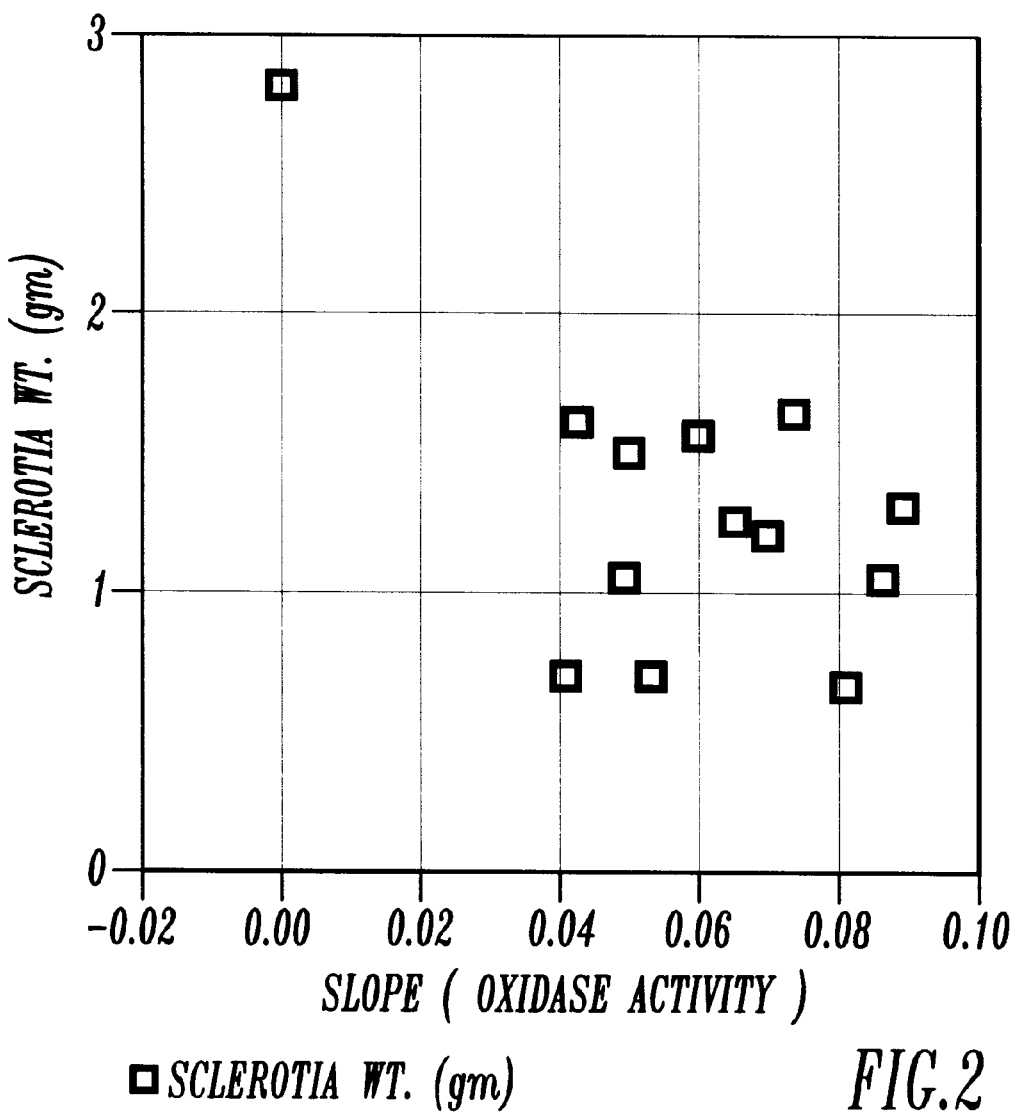
FIG. 2 shows the slope of the oxalate oxidase activity versus the sclerotia weight in sunflower.

The preferred measure of disease resistance in sunflower is sclerotia accumulation. The complex interaction of host and pathogen throughout the life cycle of both is distilled down to one measurement. The ability of the fungus to propagate itself will depend on health of the pathogen and the extent of the fungal invasion of the host. Poor disease establishment is reflected in the inability of the fungus to "reproduce." FIG. 1 shows that oxalate oxidase expression significantly reduces the number of sclerotia in oxalate oxidase expressing plants. FIG. 2 shows that oxalate oxidase expression significantly reduced the mass of sclerotia produced in oxalate oxidase expressing plants.

Figure 3:
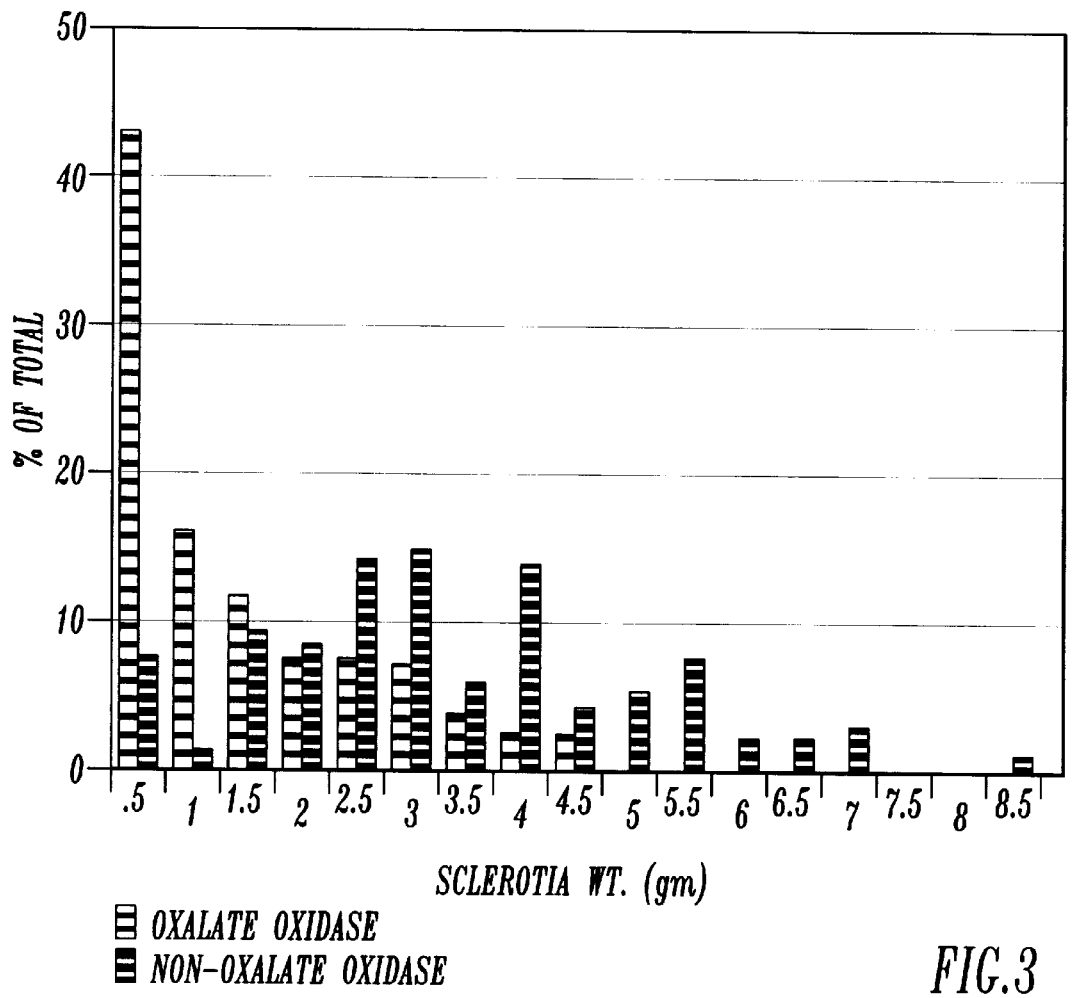
FIG. 3 shows the frequency by range of sclerotia weights in oxalate oxidase expression sunflower plants versus non-oxalate oxidase expression sunflower plants.
Figure 4:
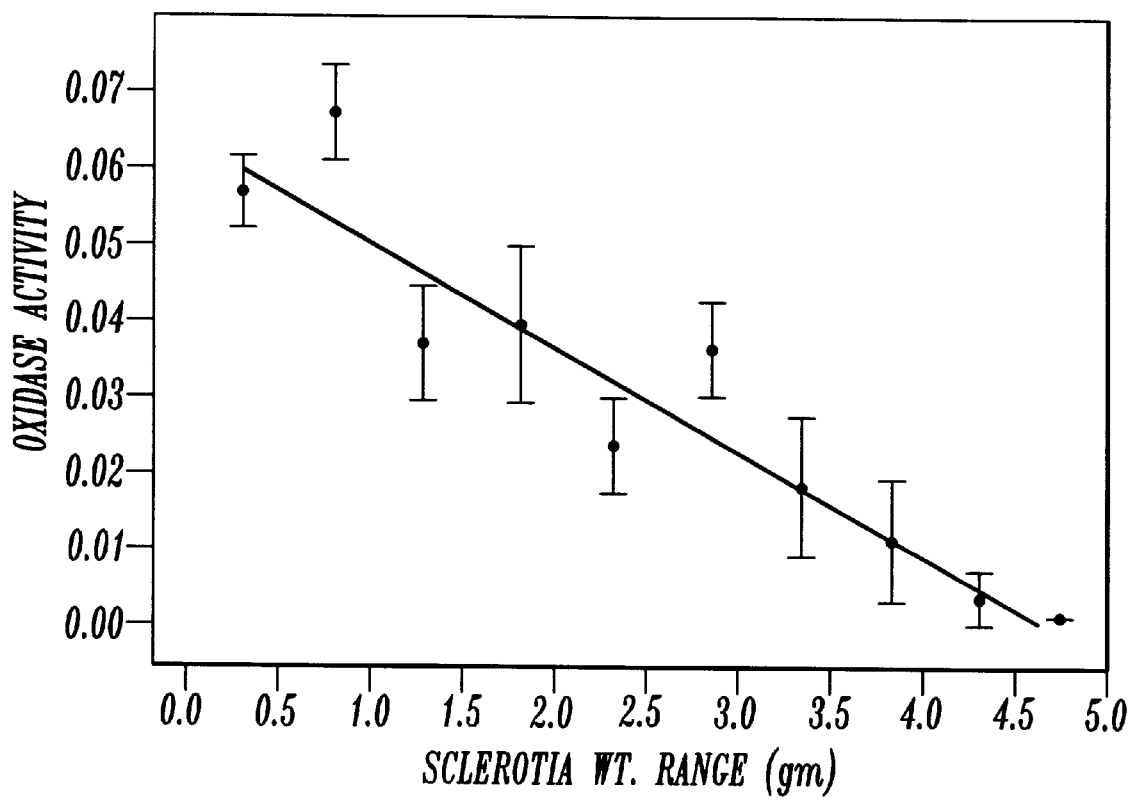
FIG. 4 shows the oxalate oxidase activity versus the sclerotia weight in sunflower plants.

FIG. 3 is the plot of the % of oxalate oxidase expressors or negative controls vs. ranges of sclerotia harvested at the end of the testing cycle and reveals the significant impact oxidase expression has on disease resistance. Clearly, FIG. 3 shows that sclerotia weights significantly decrease in oxalate oxidase expressors. In fact, the majority of oxalate oxidase expressors contained less than 0.5 gm of scelortia. FIG. 4 demonstrates the correlation of the level of oxidase activity has on sclerotia weight and thus on disease resistance. In general, the higher the oxidase expression, the less sclerotia are formed. Thus, oxidase expression prevents the formation of sclerotia.

A significant observation is that an important consequence of oxalate oxidase expression in sunflower is high levels of pathogenesis-related factors (PR) accumulate in the plants in the absence of pathogen challenge. Examples of PR factors include PR-1, chitinase, 14-3-3 protein, and glucanase. Leaf tissue was pulverized in 24 mM sodium phosphate-citrate buffer, pH 2.8 containing 6 mM L-ascorbic acid and 14 mM 2-mercaptoethanol. The homogenate was centrifuged and soluble proteins in the supernatant were analyzed by denaturing polyacrylamide electrophoresis followed by Western blotting according to Towbin, et al., *Proc. Nat'l. Acad. Sci.* (*USA*), 76: 4350 (1979) and Anderson, et al., *Electrophoresis,* 3: 135 (1982). Blots were probed with rabbit antisera raised against purified tobacco PR1b (kindly provided by Dr. Ray White, Rothamsted Experimental Station, Harpenden, Herts, UK), glucanase, 14-3-3 protein, or chitinase. Anti-glucanase and anti-chitinase sera were obtained from rabbits inoculated with *E. coli* expressed GST-glucanase or GST-chitinase fusion proteins. Arabidopsis anti-14-3-3 antibodies were uses to determine the presence of 14-3-3 protein in sunflower extracts. After incubation with primary antiserum, protein blots were treated with alkaline phosphatase-conjugated secondary antibodies, washed, and analyzed by chemiluminescence (Western-Light, Tropix). Western analysis for tobacco PR-1, chitinase, 14-3-3, and glucanase of unchallenged sunflower oxidase transgenic 193870 leaf extracts revealed significantly increased levels of all four relative to the nontransgenic control.

Salicylic acid levels in the oxidase-expressing line were also studied. Free and total (free plus conjugated) SA was extracted from 0.4 g leaf samples as previously described (Enyedi, et al., *Proc. Natl. Acad. Sci.* (*USA*), 89: 2480–2482 (1992)). Samples were analyzed with a Waters liquid chromatography system (Waters Corp., Milford, Mass). Ten microliters of each extract were injected at a flow rate of 1 ml/min into a Nova-Pak 4 μm C-18 column (3.9 cm×75 mm; Waters Corp.). The column was maintained at 40° C. and equilibrated in 22% acetonitrile against 78% of 0.1% acetic acid in water. SA was eluted isocratically under these conditions (Rt 3.1 min) and quantified using a scanning fluorescence detector (model 474, Waters Corp.) using excitation and emission wavelengths of 300 and 405 nm, respectively. The identity of SA in sunflower extracts was confirmed by its co-elution with authentic standard and by analysis of its UV light absorption spectrum, as measured with a photodiode array detector (model 996, Waters Corp.). SA levels in the oxidase-expressing line were 6 fold that of the control.

Figure 5:
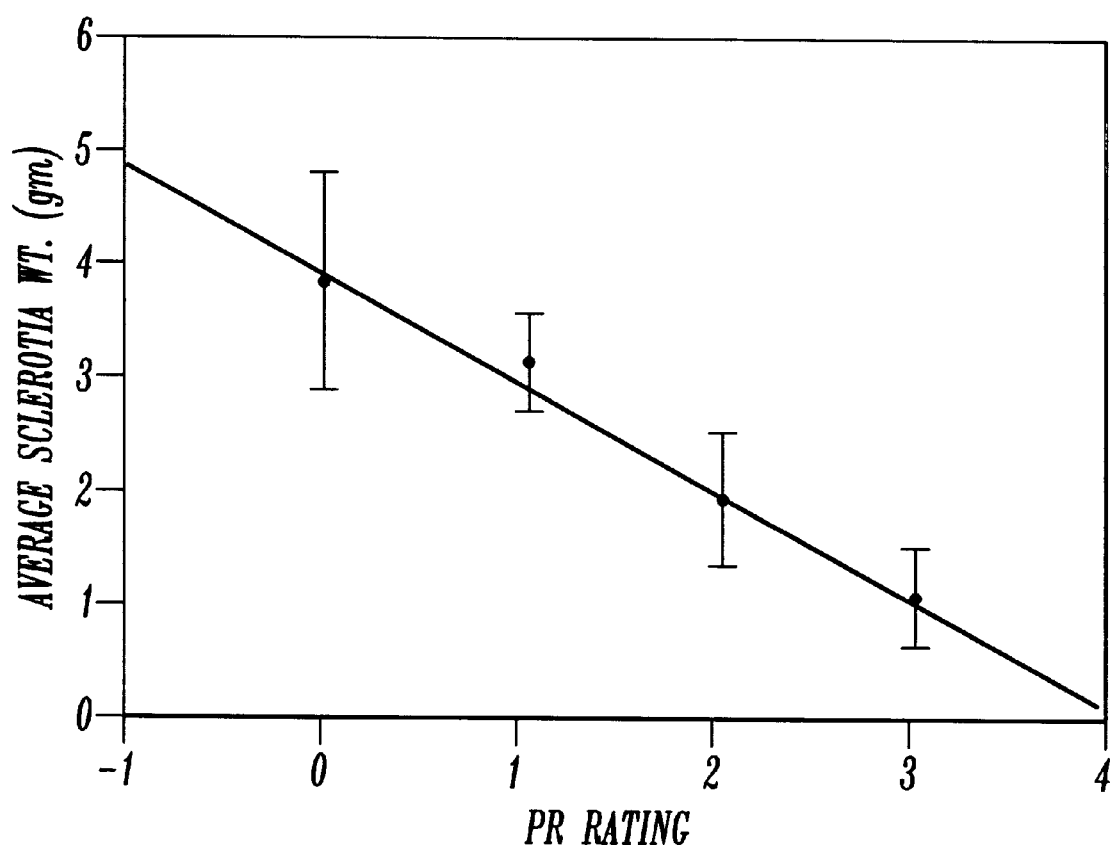
FIG. 5 is a graph of sclerotia weight versus PR protein expression in sunflower plants.
Figure 6:
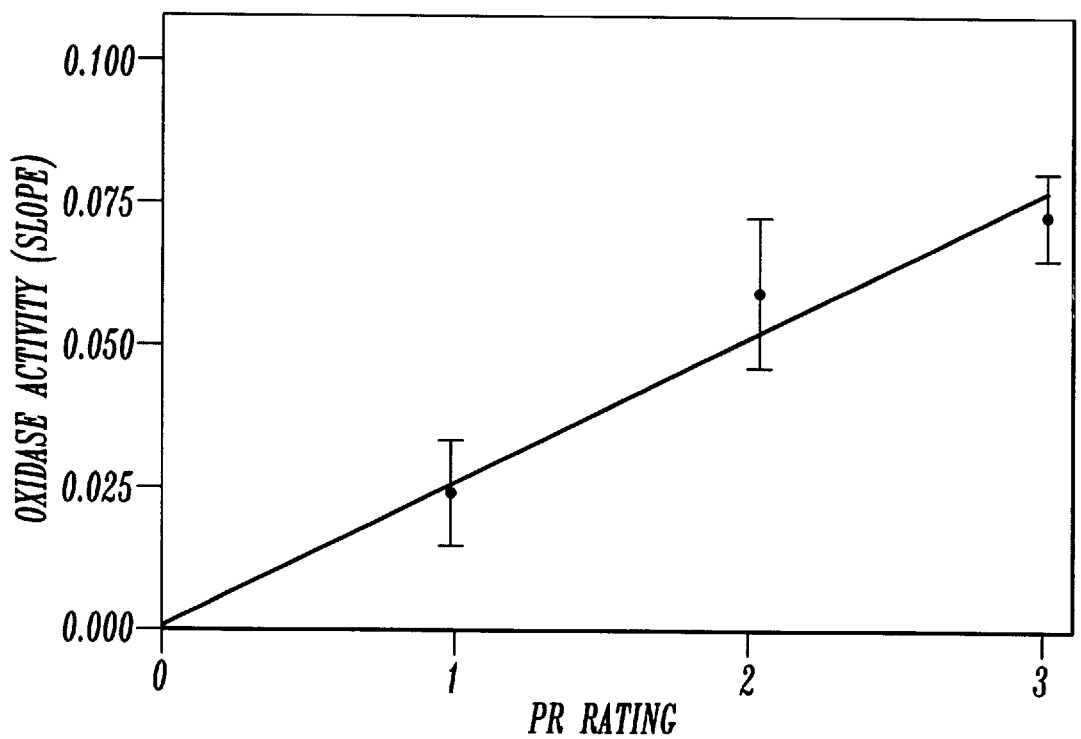
FIG. 6 is a graph of the slope of the oxidase activity versus the PR protein rating in sunflower plants.

A larger set of leaf samples from the prior greenhouse evaluations were examined for PR-1 levels and expression and quantified by assigning a 0 thorough 3+ for the banding intensity. This information was plotted vs. sclerotia accumulation to determine if increased levels of PR protein would be useful as a disease resistance predictor. (FIG. 5) It seems clear that PR-1 is present during disease resistance and that oxalate oxidase expression is able to induce this factor through the generation of hydrogen peroxide by the degradation of cellular, not fungal, substrate. Other observations are that the PR-1 rating of 1+ is not significant from 0, 75% of the oxidase transgenics have PR-1 ratings of 2+ or 3+, and 70% of the non-oxidase controls have PR-1 ratings of 0 or 1+. In addition when oxidase activity is plotted against the PR-1 ratings (FIG. 7), a direct correlation between oxalate oxidase levels and PR-1 protein amounts can be seen. Increased expression of oxidase oxalate causes the level of PR-1 protein to also increase.

To address the relationship between oxalate oxidase activity, SA levels and PR protein levels, a time course study was carried out with two transgenic lines of sunflower expressing oxalate oxidase (193870—1X35S::oxalate oxidase and 610255—SCP1::oxalate oxidase). The results consistently showed that oxalate oxidase activity rapidly increased to a high level (greater than 300 μM/Min.mg) within 4 weeks from germination in transgenic plants. No activity was detected in control SMF3 seedlings. From 2 to 4 weeks SA and PR-1 levels are similar to control plants. Yet by 6 weeks in transgenic plants a 2–4 fold increase in the level of SA and PR-1 can be seen as compared to controls. At 6 weeks from germination both SA and PR-1 were significantly induced in oxalate oxidase expressing plants in the absence of pathogen challenge.

The function of PR-1 protein is largely unknown. To determine the possible effect of PR-1 protein on Sclerotinia, an in vitro assay using purified tobacco PR-1 was carried out. A suspension of 300 Sclerotinia spores in 100 μl of a solution of 13% sucrose, with or without PR-1, was placed in a micro-plate. The spores were incubated at room temperature for 24 hours. Following the 24 hour incubation the micro-plates were examined microscopically. Germination was defined as the appearance of *Sclerotinia hyphae* in the suspension. At 1.6 μM PR-1b minimal inhibition was observed. At 4.9 μM PR-1b no hyphal growth was found and complete inhibition was seen. Thus, induction of PR-1 in a plant will restrict Sclerotinia spore germination.

Oxalate Decarboxylase Expression in Sunflower Transgenics

The oxalate decarboxylase gene isolated from Flammulina (WO 94/12622 published in Jun. 9, 1994 and hereby incorporated by reference) was introduced into sunflower, as described earlier, and Sclerotinia disease screenings were performed using the same protocols of inoculation and rating employed for oxidase transgenics. Optionally, another gene for oxalate decarboxylase can be used. The oxalate decarboxylase gene isolated from *Aspergillus phoenices* (U.S. patent application Ser. No. 08/821,827, filed on Mar. 21, 1997) may also be used in the present invention. Expression of oxalate decarboxylase in transformed plant cells and tissues can be detected by the enzyme assay described by Labrou, et al., *J. Biotech*, 40: 59–70 (1995); and Johnson, et al., *Biochem. Biophys. Acta* 89:351 (1964). Decarboxylase activity is linked to a second activity, that of formate dehydrogenase, that will oxidize the decarboxylase generated formate with the subsequent reduction of NAD to NADH (Johnson, et al., *Biochem Biophys. Acta* 89:351 (1964)). The increase of OD340 as NAD is reduced is used to generate an initial reaction rate that is linear with respect to formate concentration from 0.2 to 2.0 umole. The assay was adapted to megatiter plates so that a large number of samples could be screened. Leaf tissue samples were prepared and assays set up as in the oxalate oxidase assay protocol except that the decarboxylase reactions were run from 1 to 3 hours. Following the assay period, 100 μl of each reaction supernatant were transferred to microtitre plate wells and 17.5 μl of 1M Tris free base solution was added to each. Next 10 μl of b-NAD (6.6 mg/ml stock, Sigma) are added to each sample well and mixed followed by the addition of 5 μl of formate dehydrogenase (4.0 mg/ml stock, 1 enzyme unit/mg solid, Sigma). The absorbance at 340 nm was measured repeatedly over a 10 minute period to generate a reaction rate curve. The slope of the initial rate curve was determined.

Replicated greenhouse disease screens of several Flammulina decarboxylase-expressing transgenics demonstrated that decarboxylase metabolism of oxalate is an effective deterrent to Sclerotinia disease progression in sunflower, as can be seen in Table 2.

TABLE 2

| Line | Gene | Sclerotia wt. Avg. (gm) |
| --- | --- | --- |
| 436741 | decarboxylase | 0.43 |
| 436747 | decarboxylase | 0.65 |
| 436784 | decarboxylase | 1.14 |
| 436705 | decarboxylase | 0.13 |
| 436724 | decarboxylase | 0.43 |
| 460078 | decarboxylase | 0.95 |
| 193870 | oxidase | 0 |
| SMF-3 | control | 0.73 |

Figure 7:
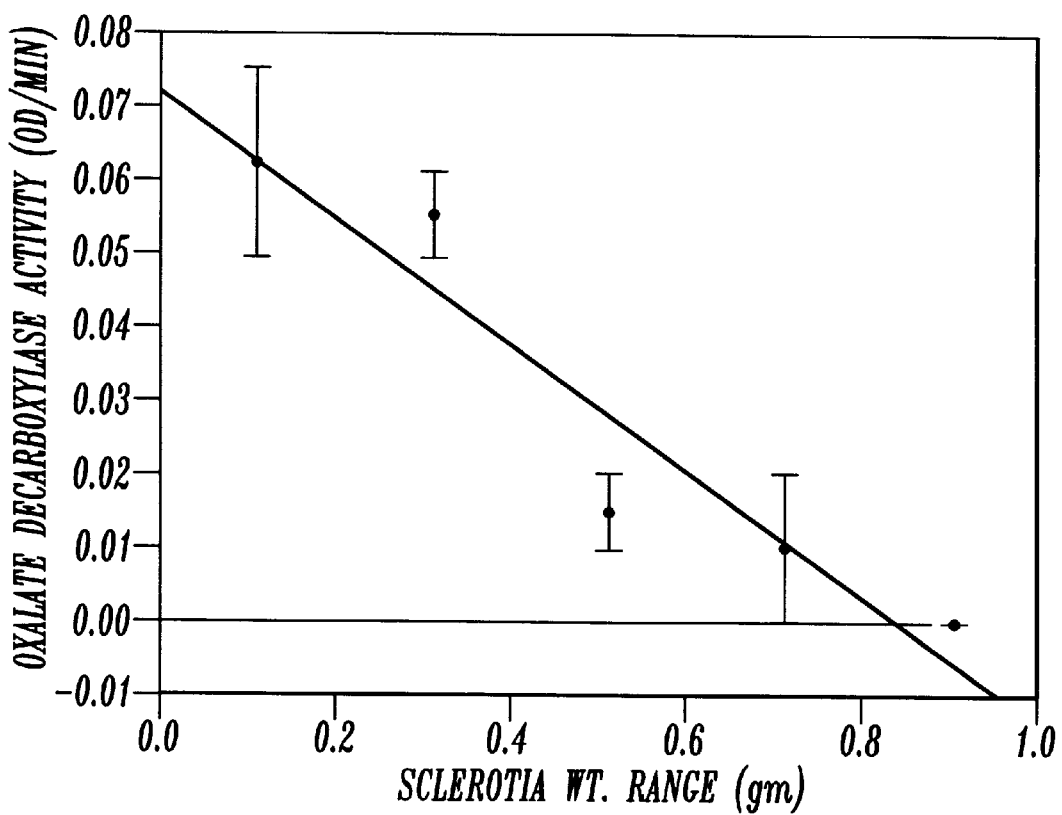
FIG. 7 is a graph of the slope of the oxalate decarboxylase enzyme activity versus the sclerotia weight in sunflower plants.
Figure 8:
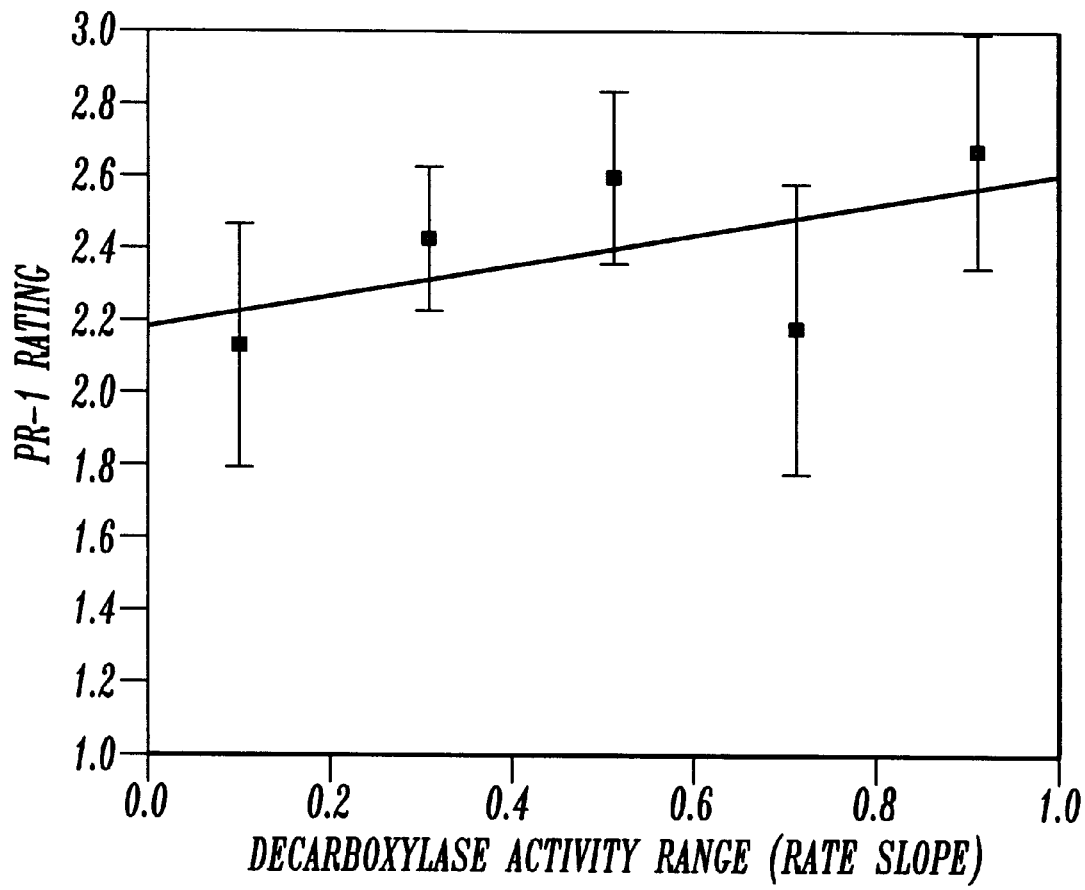
FIG. 8 is a graph of the oxalate decarboxylase activity range versus PR rating.

The correlation of decarboxylase activity with sclerotia accumulation is presented in FIG. 7. In general, the higher the expression of decarboxylase the less sclerotia are formed. In order to understand the role of oxalate degradation and the generation of the disease response, oxalate decarboxylase transgenic material was tested for the presence of PR-1 proteins as previously described. As can be seen in FIG. 8 there is little correlation between oxalate decarboxylase activity and the presence of PR-1. Thus, degradation of oxalate by oxalate decarboxylase does prevent Sclerotinia disease progress, but does not initiate the disease response pathway as seen in oxalate oxidase transgenic plants.

Combining Conventionally Tolerant Sunflower Lines with Oxalate Oxidase or Oxalate Decarboxylase Expressors In order to cross the oxalate oxidase or oxalate decarboxylase gene into conventionally tolerant sunflower lines, the following procedure was performed. Pollen was collected from the best challenged event, 193870. A single head from 8 different elite lines were selected and hand emasculated daily. This entails removing the anthers from the ring of flowers that emerge each day and rinsing with water to ensure no pollen remains that could self-pollinate. This procedure was done for 3–4 days upon which time the center of the head is cut out, leaving no more flowers to emasculate. The pollen, from the donor plant was collected on a paper towel, crossing paper and then rubbed on the emasculated heads. All flowering heads were bagged before and after any crossing. The resulting progeny were grown in the greenhouse and tested for resistance to Sclerotinia and evidence of the lesion mimic phenotype.

Figure 9:
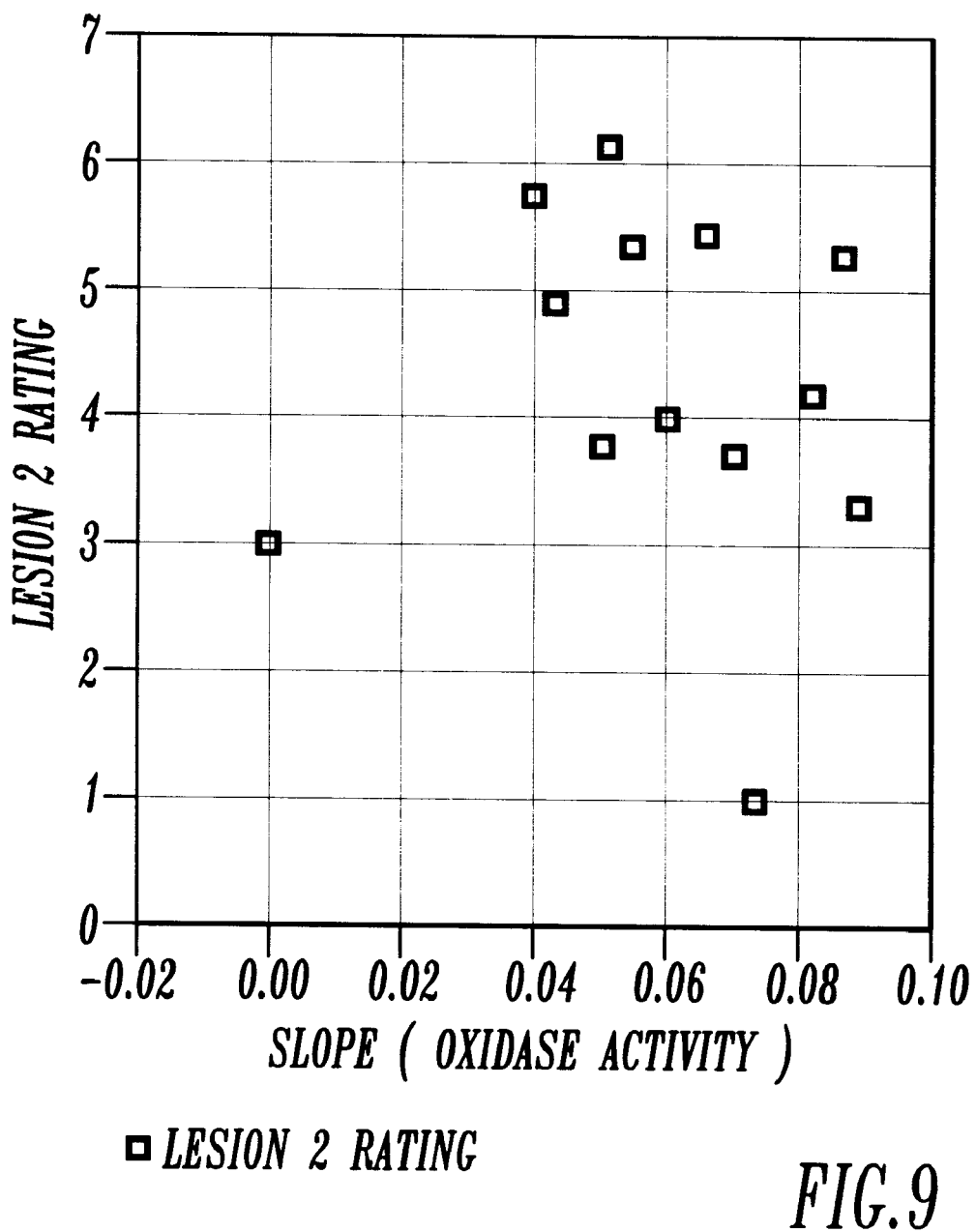
FIG. 9 shows the slope of the oxalate oxidase activity versus the fungal lesion rating.

Oxalate oxidase-produced hydrogen peroxide induces the accumulation of factors associated with resistance to stress even though challenges such as pathogen attack are not present. Unfortunately, one of the side effects of a continuous, unregulated expression of resistance factors is a lesion mimic phenotype. Sunflower oxalate oxidase expressing plants show numerous necrotic lesions on their leaves. In FIG. 9 the oxidase activity in transgenic plants is compared to the lesion rating. The data points are the averages over 4 replications performed throughout the year. The ratings are as follows: 1=susceptible, up to 9=resistant. In non-transgenic plants lesions are a sign of a disease infection. In the case of oxalate oxidase expressing transgenics, that were highly resistant to disease, there were still a large number of lesions.

By crossing oxalate oxidase expressing plants with germplasm showing tolerance to Sclerotinia a sunflower plant with immunity to Sclerotinia and no lesion mimic phenotypes were produced. The combination of oxalate oxidase expression in a tolerant germplasm background causes a synergistic effect of a superior plant which is far better than either of its parents. Table 3 summarizes the data for this set of experiments. PR126M and PR118M are both sunflower lines which show tolerance to Sclerotinia. PK93M and PK68F are susceptible to Sclerotinia infections.

TABLE 3

| Line | oxox Activity | Lesion Rating | Sclerotia wt. (gm) | # |
|---|---|---|---|---|
| transgenic 193870 | 0.082 | 7.1 | 0.8 | 27 |
| PR126M(T) x 193870 | 0.073 | 8.0 | 0 | 0 |
| PR118M(T) x 193870 | 0.065 | 8.3 | 0 | 0 |
| PK93M (S) x 193870 | 0.066 | 6.3 | 1.0 | 48 |
| PK68F (S) x 193870 | 0.049 | 3.5 | 2.0 | 66 |

As can be seen in Table 3, all the plants showed comparable levels of oxalate oxidase expression, yet there were no Sclerotia formed in the oxalate oxidase expressors crossed with tolerant germplasm. In addition, the lesion levels were the least for the oxalate oxidase expressors crossed with tolerant germplasm. In the absence of Sclerotinia infection the oxalate oxidase expressors crossed with the tolerant germplasm plants exhibited a normal leaf phenotype with no necrotic lesions. Thus, the synergistic effect of oxalate expression and tolerance genetics produces a commercial quality plant, immune to Sclerotinia infection but with no negative phenotypes.

In order to demonstrate that the greater resistance of the transgenic, Sclerotinia tolerant sunflower is the result of the presence of the oxalate oxidase gene, the four lines listed in Table 3 were used in genetic crosses designed to create equivalent materials which contain or lack the transgene. The Sclerotinia inoculations were done using the same technique as that described to generate the data in Table 3. The test was allowed to proceed to the end of the sunflower life cycle at which time the dried stalks were obtained and individually split open in order to isolate Sclerotinia sclerotial bodies. A more invasive or extensive mycelial mass in an infected plant is an indication of a more successful infection and leads to increased sclerotial body production. The sclerotial body number and total weight were used to measure the biological success and reproductive fitness of Sclerotinia and, therefore, of the ability of sunflower lines to inhibit disease progression and decrease fitness.

Figure 10:
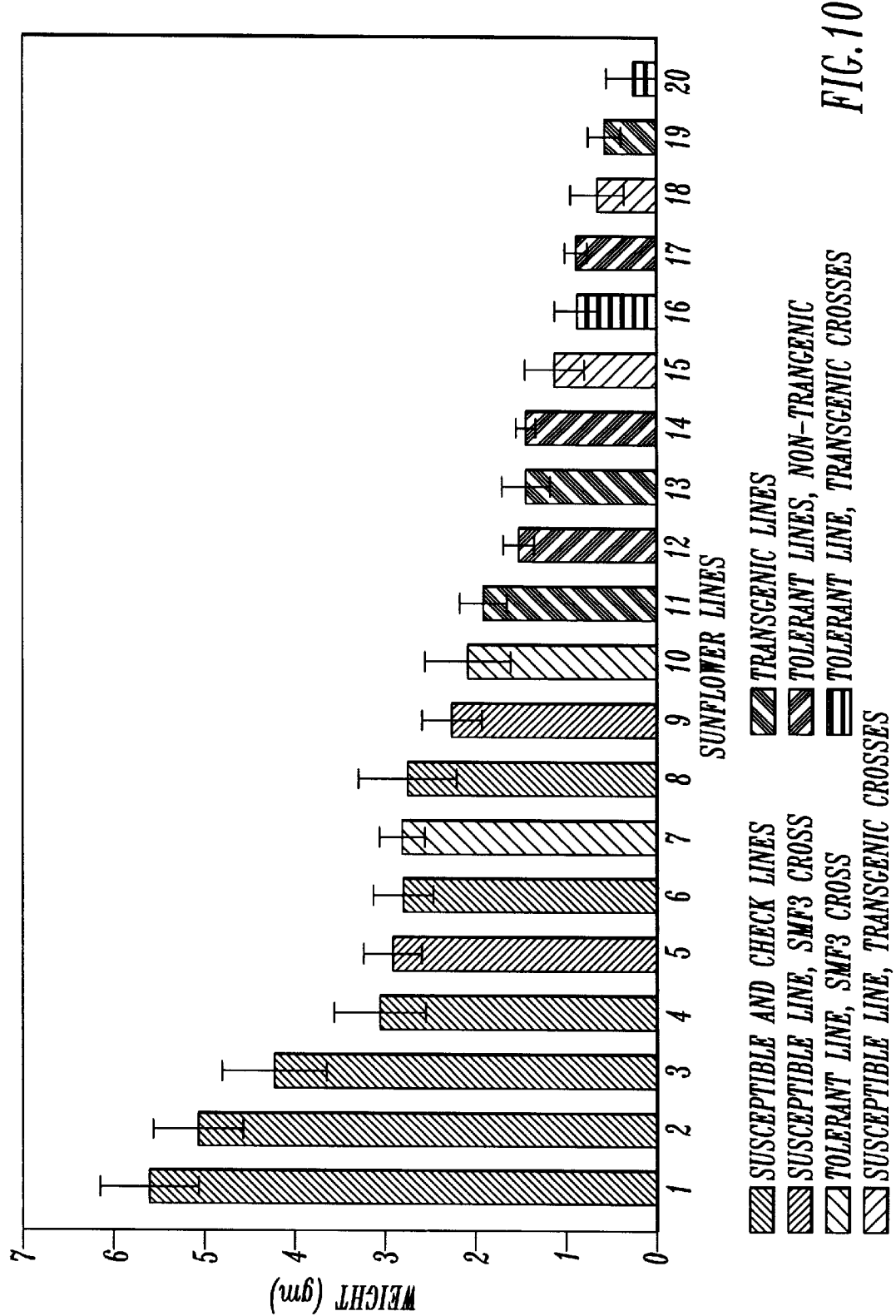
FIG. 10 shows sclerotial body weight comparisons of various sunflower varieties. *Sclerotinia sclerotiorum* inoculated sunflower lines were allowed to complete their life cycle and then harvested in order to collect and measure sclerotial bodies. The resistance or susceptibility and presence or absence of the transgene are indicated by the different bars and numbers. The number labeling each bar corresponds to the specific genotype and whether or not it is trangenic according to Table 4.
Figure 11:
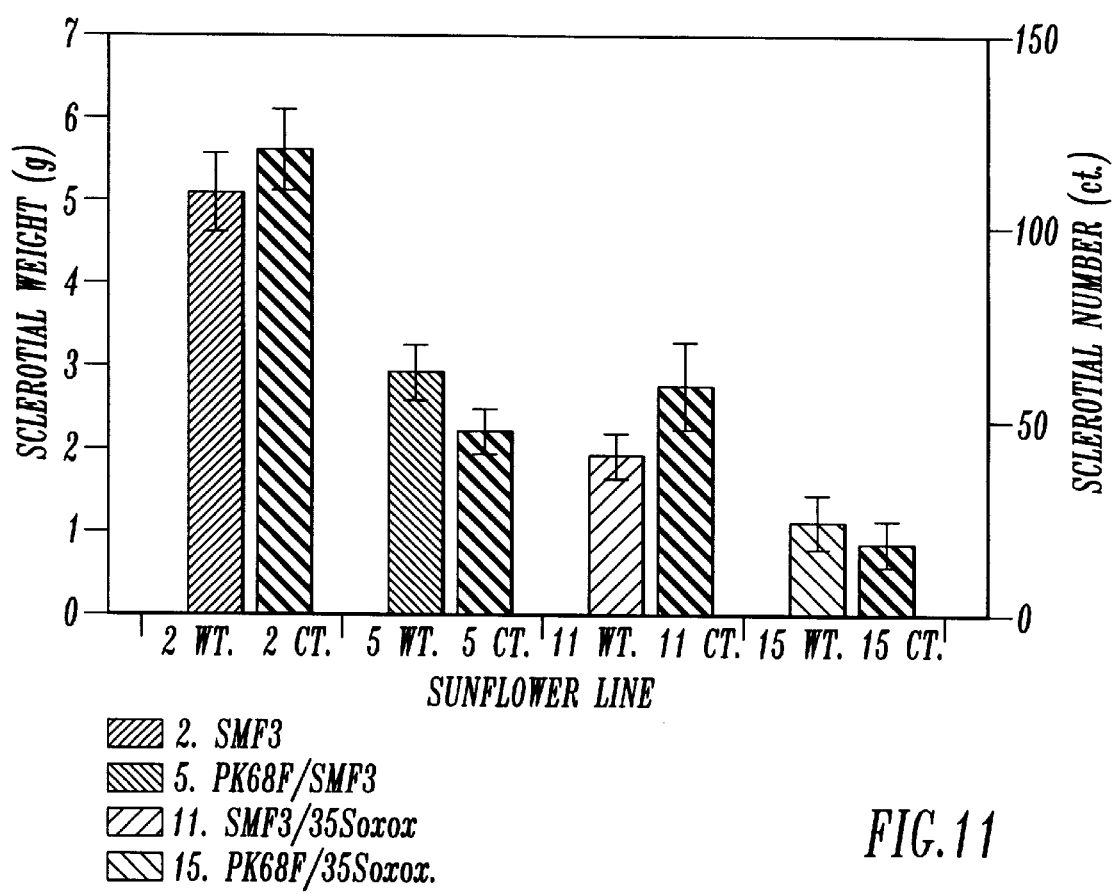
FIG. 11 shows the effect of sunflower line PK68F and the expression of oxalate oxidase on *Sclerotinia sclerotiorum* sclerotial body weight and number. Data is presented which separates the lines into appropriate comparisons; each of the non-transgenic parent lines, the non-transgenic hybrids (PK68F/SMF3, PK93M/SMF3, PR118M/SMF3 and PR126M/SMF3), transgenic SMF3 event 193870 (SMF3/35Soxox), and the transgenic hybrid with SMF3 event 193870 (PK68F/35Soxox, PK93M/35Soxox, PR118M/35Soxox, and PR126M/35Soxox). Numerical identification, listed under the bars in each graph, correspond to those presented in the table associated with Table 4. (abbreviations: wt.—weight, ct.—count, oxox=oxalate oxidase, 35S=35S promoter)
Figure 12:
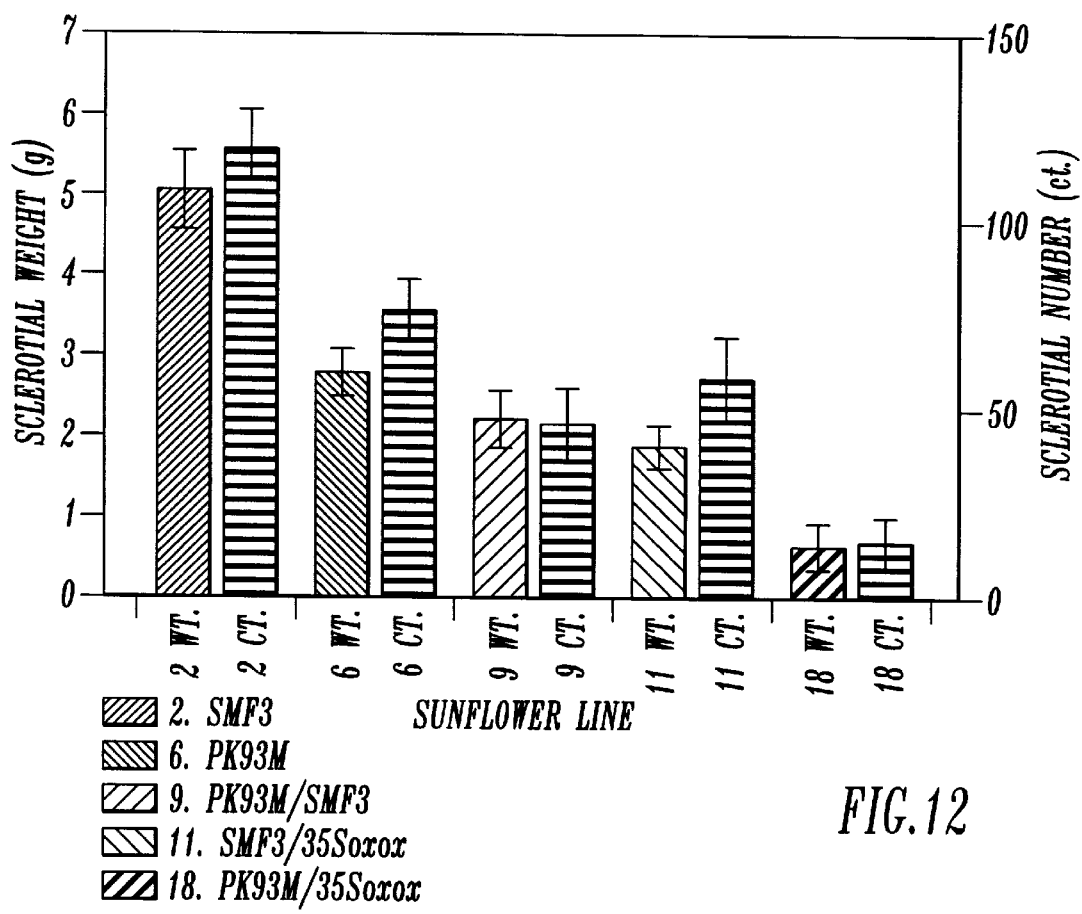
FIG. 12 shows the effect of sunflower line PK93M and the expression of oxalate oxidase on *Sclerotinia sclerotiorum* sclerotial body weight and number. Data is presented which separates the lines into appropriate comparisons; each of the non-transgenic parent lines, the non-transgenic hybrids (PK68F/SMF3, PK93M/SMF3, PR118M/SMF3 and PR126M/SMF3), transgenic SMF3 event 193870 (SMF3/35Soxox), and the transgenic hybrid with SMF3 event 193870 (PK68F/35Soxox, PK93M/35Soxox, PR118M/35Soxox, and PR126M/35Soxox). Numerical identification, listed under the bars in each graph, correspond to those presented in the table associated with Table 4. (abbreviations: wt.—weight, ct.—count, oxox=oxalate oxidase, 35S=35S promoter)
Figure 13:
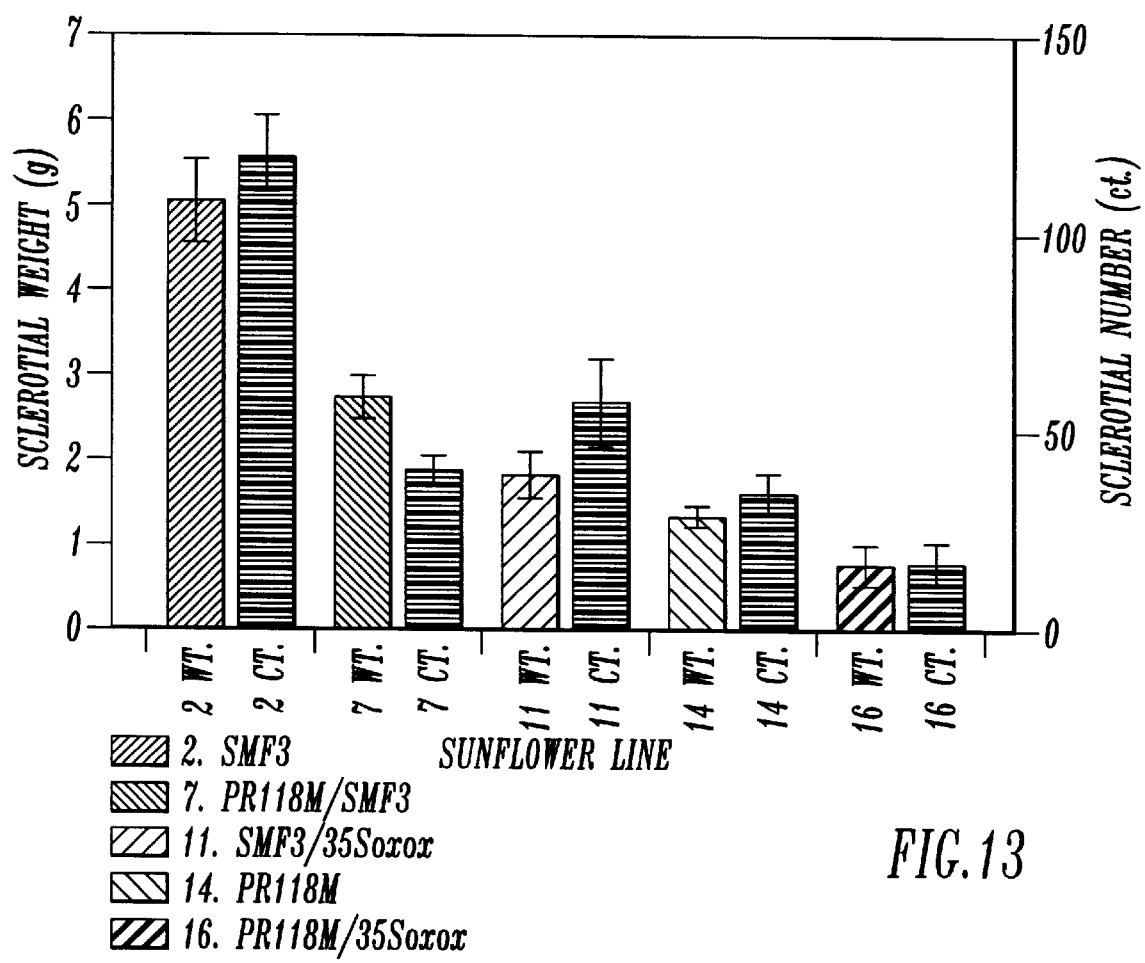
FIG. 13 shows the effect of sunflower line PR118M and the expression of oxalate oxidase on *Sclerotinia sclerotio-*

FIG. 10 presents the sclerotial body weights from all of the lines tested. Each bar on the bar graph represents the mean and standard error of eight individual plants. The individual plants are described in the following Table 4. The numbers labeling each bar of FIG. 10 correspond to the specific genotype and whether or not it is transgenic according to the Table 4.

TABLE 4

| Number | Line | Number | Line |
|---|---|---|---|
| 1. | Susceptible Check 1 | 11. | Event 193870 (SMF3 transgenic) |
| 2. | SMF3 (sus*) | 12. | PK68G (sus) |
| 3. | SMF3 (sus) | 13. | Event 610255 (SMF3 transgenic) |
| 4. | USDA 894 (sus) | 14. | PR118M (tol) |
| 5. | PK68F (sus) X SMF3 | 15. | PK68F (sus) X 193870 |
| 6. | PK93M (sus) | 16. | PR118M (tol) X 193870 |
| 7. | PR118M (tol#) X SMF3 | 17. | PR126M (tol) |
| | | 18. | PK93M (sus) X 193870 |
| 8. | Susceptible Check 2 | 19. | Event 539149 (SMF3 transgenic) |
| 9. | PK93M (sus) X SMF3 | 20. | PR126M (tol) X 193870 |
| 10. | PR126M (tol) X SMF3 | | |

*sus - susceptible to Sclerotinia infection. # tol - tolerant to Sclerotinia infection.

Data presented in this graph directly support conclusions made from data presented in Table 3. Most importantly, the genetic Sclerotinia tolerance combined with the oxalate oxidase transgene gave a near immune response to this pathogen (see FIG. 10, bars 16 and 20) which is superior to the resistance of either parent. The increased resistance was not due to higher oxalate oxidase enzyme activity since the susceptible and tolerant line crosses with 193870 gave comparable activity levels (Table 5). In fact, 193870 is a homozygous line and demonstrated about twice the activity of the heterozygous crosses. Susceptible check lines showed the highest sclerotial body weights because the fungus growth was relatively uninhibited (FIG. 10). Tolerant lines, transgenic lines, and susceptible lines crossed with event 193870 were superior to non-transgenic susceptible lines, and susceptible or tolerant lines crossed with non-transgenic SMF3.

TABLE 5

Oxalate oxidase enzyme activity in transgenic SMF3 plants and in hybrid plants resulting from genetic crosses between SMF3 and Sclerolinia susceptible or tolerant parents.

| Line | Genetic Status | Parent Line | Oxalate oxidase activity (OD550/mg/hr) |
|---|---|---|---|
| Event 193870 | homozygous | Susceptible | 53 |
| Bvent 610255 | homozygous | Susceptible | 66 |
| PK68F X 193870 | heterozygous | Susceptible | 22 |
| PK93M X 193870 | heterozygous | Susceptible | 29 |
| PR118M X 193870 | heterozygous | Tolerant | 30 |
| PR126M X 193870 | heterozygous | Tolerant | 30 |

When non-transgenic hybrids are compared to parental lines some differences in the line contribution to resistance can be observed. Both tolerant line hybrids showed greater sclerotial body weights than the parental tolerant line alone, suggesting that the cross with SMF3 may have reduced their ability to resist Sclerotinia (FIGS. 11–14). The PK93M hybrid had a similar to slightly reduced sclerotial weight value compared to parental line PK93M. In this case, there may be a slight contribution to resistance made by SMF3 or perhaps hybrid vigor. The same case might be made for the non-transgenic hybrid with parental line PK68F. This hybrid has significantly lower values than the SMF3 parent. The PK68F parental line, however, was not included as a control in that data set so no direct comparison could be made. Parental line SMF3 had higher sclerotial body weights and numbers than any of the other lines to which it was crossed. These comparisons suggest that there may be a slight SMF3 contribution to Sclerotinia resistance in the susceptible line hybrids but that it may actually reduce resistance in the tolerant lines.

Comparisons made between transgenic SMF3 event 193870 (SMF3/35Soxox in FIGS. 11–14) and the parental non-transgenic lines show that it is the superior line for resistance compared to susceptible line PK93M, but that the Sclerotinia tolerant, non-transgenic parents are more resistant. When compared to non-transgenic SMF3 it is clear that the oxalate oxidase transgene contributes significantly to resistance. There may be conventional genetics which are more resistant to Sclerotinia than oxalate oxidase transgenic SMF3, but FIGS. 11–14 demonstrate that the presence of this transgene enhances resistance in every line in which it was introduced. When combined with the tolerant genetics of PR126M, oxalate oxidase conferred nearly complete immunity to Sclerotinia (FIGS. 11–14). Six out of the eight PR126M/193870 plants had no sclerotial bodies at all (data not shown). The resistance of this line surpassed all of the others presented in spite of the fact that it has lower enzyme activity than 193870 and that SMF3 may detract from the genetic resistance. This data confirms the synergistic effect of the oxalate oxidase gene and Sclerotinia tolerant genetics.

Transgenic oxalate decarboxylase expressing plants are crossed as described above, into conventionally tolerant backgrounds. Oxalate decarboxylase expressing plants are tested for resistance to Sclerotinia as described earlier.

Example 2

Canola

Sclerotinia stem rot is a disease of *Brassica napus*, *Brassica rapa* and *Brassica juncea* caused by the fungus *Sclerotinia sclerotiorum*. Sclerotinia stem rot is also found in more than 400 other dicots. The disease results in premature ripening and seed shriveling in the field. Canola is a Brassica rapeseed crop with low glucosinolates and low erucic acid content. All cultivars/hybrids of canola quality grown worldwide are susceptible to this disease. Brun, H., et al., pp. 1216–1221. *Proceedings of the 7$^{th}$ International Congress on Rapeseed, Poznan,* (1987).

Partial conventional tolerance was found in Asiatic germplasm. Current attempts to transfer this tolerance into canola quality material and attain enhanced tolerance have been unsuccessful, primarily due to the complexity of the disease, a low tolerance level and a hardship in screening to detect tolerance in breeding programs. Another approach taken was to transform canola plants with the oxalate oxidase gene which degrades oxalic acid generated by the fungus into hydrogen peroxide and carbon dioxide. For the first time an enhanced level of tolerance to the fungus was seen in the F1's generated from crosses of a conventionally tolerant canola quality line and a transgenic line containing the oxalate oxidase gene.

Canola Transformation Protocol

The following is a standard procedure of Agrobacterium (strain LBA4404) mediated cotyledonary transformation (Moloney, M. et al., *Plant Cell Rep.,* 8: 238–242 (1989)) used to produce 16 pPHP7746 and 64 pPHP8188 transgenics *B. napus* Pioneer variety 46A65.

1. Sowing seed for experiments
 1. Place approximately 250 seeds in seed sterilization apparatus.
 2. Spray seeds with 70% ETOH.
 3. Place seed apparatus in 2% sodium hypochlorite solution (30% commercial bleach solution) and let sit for 15 minutes, stirring occasionally to ensure seeds are thoroughly soaked.
 4. Place seed apparatus in sterile water for 5 minutes to rinse off bleach from the seeds.
 5. Empty out seeds into a sterile petri dish.
 6. Plate seeds onto GM (germination medium) (Murashige and Skoog salts (MS salts, Gibco) 10 mls/liter of MS supplements for organics (in 1 liter, 10 g of l-inositol, 40 mg Thiamine-Hcl and 100 g MES), 3% sucrose, pH 5.8, and 0.2% gelrite), at 10–12 seeds/plate. Box plates. Place box in 10° C. to synchronize germination or may place directly in 24° C. (tissue culture room).
 7. Seedlings ready for cocultivation in 4–6 days (dependent on cultivar).
2. Grow Agrobacterium containing gene of interest
 1. Obtain Agrobacterium with gene of interest from vector construction provider. Used pPHP7746 and pPHP8188.
 2. Prepare bacterial overnight culture 1 day prior to cocultivation, by culturing 10 ul loop of Agrobacterium in 15–30 ml of LB broth (GIBCO) supplemented with appropriate antibiotics and 200 uM acetosyringone.
 3. Place culture tube/flask in 28 C shaker at 200 rpm.
 4. On day of cocultivation, centrifuge the bacterial suspension at 2000–3000 rpm for 10 minutes.
 5. Discard supernatant and then resuspend bacterial pellet in 15–40 ml of MS-H medium (MS salts (Gibco) 10 ml/liter MS supplements for organics (see above), 2% sucrose, and pH 5.7) containing 200 uM acetosyringone.
 6. Decant suspension into 30 ml sterile petri dishes, between 5–15 ml/dish.
3. Napus: Cocultivation
 1. Excise cotyledons such that as much of the petiole is intact as possible without including the meristems.
 2. Plate 1 non-inoculated control plate, using 10–12 cotyledons, with the remaining cotyledons, dip the cotyledonary petiole (cut end) into the bacterial suspension (2.6)

3. Plate the inoculated cotyledons on MMW media (MS salts (Gibco), 10 ml/liter MS supplement for organics (see above), 3% sucrose, 4.5 mg benzladeninepurine (1st dissolved is the least possible amount of methanol), 0.1 mg/liter abscissic acid, pH 5.8, and 6% agar (Sigma #1296) at 20–30 cotyledons/plate.
4. Wrap all plates with surgical tape, and place in transparent box in tissue culture room at 24 C, for 2–3 days with 16 hour photoperiod.

Transfer cotyledons as follows:
1. Non-inoculated control—5–6 cotyledons on MMW media (MS salts (Gibco), 10 ml/liter MS supplement for organics (see above), 3% sucrose, 4.5 mg benzladeninepurine (First dissolved is the least possible amount of methanol), 0.1 mg/liter abscissic acid, pH 5.8, and 6% agar (Sigma #1296)+carbenicillin 300–500 mg/L, and on MMW+ carbenicillin 300–500 mg/L+selection agent. (Kan 100 mg/L for pPHP7746 and Glufosinate 4 mg/L for pPHP8188)
2. Inoculated control—5–6 cotyledons on MMW+ carbenicillin (carb) 300–500 mg/L
3. All remaining cotyledons—plated on MMW+carb 300–500 mg/L+selection agent (see above)
4. All plates are sealed with surgical tape, boxed, and place in tissue culture room for 3 weeks.

Second transfer to shoot selection media:
1. Transfer cotyledons onto media as above. Seal plates, box and culture for an additional 3 weeks, or until shoots form from cut end.
2. Excise green, healthy shoots and place on B5-H H (see media recipe below)+carb 300–500 mg/L+selection agent media. This media allows rooting.
3. If shoots have rooted, assay for reporter gene activity.
4. After analysis, transplant confirmed transgenic shoots to soil.

| B6-H | |
|---|---|
| Media Ingredients Combine: | 5 LITERS |
| B5 x5 stock | 1 L |
| Sucrose (2%) | 100 g |
| USE filtered H$_2$O to up volume to 5 L | |
| Phytagel (Sigma #p8169) | 20 g |
| pH solution to 5.8 | |

Autoclave

After Autoclaving: Add appropriate selective agents or plant hormones

| B5 Bx Stock | |
|---|---|
| Stock Ingredients Combine: | 4 LITERS |
| Potassium Nitrate (kNO$_3$) | 50.0 g |
| Magnesium Sulphate (MgSO$_4$—7H$_2$O) | 5.00 g |
| Calcium Chloride Dihydrate (CaCl$_2$2H$_2$O) | 15.00 g |
| Ammonium Sulphate ((NH$_4$)$_2$SO$_4$) | 2.68 g |
| Sodium Phosphate Monobasic (NaH$_2$PO$_4$—H$_2$O) | 3.00 g |
| Iron 330 (Fe330) | 0.80 g |
| B5 Vitamin Stock (100x) | 200 mls |
| B5 Micronutrients (100x) | 200 mls |
| Potassium Iodide Stock | 20 mls |

Bring up the volume to 4 L with filtered water

| B5 Vitamin Stock (100x) | |
|---|---|
| Ingredient Combine: | 1 LITER |
| Myo-inositol | 10.0 g |
| Nicotinic Acid | 100.0 mg |
| Pyridoxine HCL | 100.0 mg |
| Thiamine HCL | 1.0 g |

Bring up the volume to 1 L with filtered water

| Micronutrient Stock Solution (1000x) | |
|---|---|
| Ingredient Combine: | 1 LITER |
| Manganous Sulphate (MnSO$_4$—H$_2$O) | 10.0 g |
| Boric Acid (H$_3$BO$_3$) | 3.0 g |
| Zinc Sulphate-7 Hydrate (ZnSO$_4$—7H$_2$O) | 2.0 g |
| Sodium Molybdate (Na$_2$MoO$_4$—2H$_2$O) | 250.0 mg |
| Cupric Sulphate-5 Hydrate (CuSO$_4$—5H$_2$O) | 25.0 mg |
| Cobalt Chloride-6 Hydrate (CoCl$_2$—6H$_2$O) | 25.0 mg |

Bring up the volume to 1 L with filtered water
Make to 100x before using by:
   Adding 100 ml of 100x and bringing it up to a 1 Liter volume by adding 900 ml of filtered water
Potassium Iodide (Kl) Solution
   Add 0.83 g of KI in 1 liter of filtered water.

Two of the sixteen transgenics were single copy integration events. Progeny (T1) from these single events along with three double copy lines and two multiple copy lines underwent greenhouse Sclerotinia screening. Results from the indoor screening showed the double copy line 170B3 and single copy line 164B1 were more disease tolerant than their non-transformed parent line NS1565. Oxidase assays results on the T2 transgenic plants screened showed 170B3 and 164B1 plants had the highest and second highest expression levels respectively when compared against the other T1 lines tested. The 164B1 and 170B3 T2 lines were field tested.

Field Screening of Oxalate Oxidase Canola Transgenics

Field trials were conducted at the Stirk's site in Hillsburg, Ontario, Canada. The level of background inoculum was high and it was assessed by visual estimate of the presence of apothecia and by doing a petal test. A petal test is performed by placing canola petals on Potato Dextrose Agar or other media for growth of Sclerotinia sclerotiorum, in order to determine if they are infested with the fungus. Since infection of canola with the fungus occurs only by infested petals, this test reveals if and to what extent the fungus is present in the field. Other than the presence of the fungus, favorable environmental conditions and the presence of susceptible host are critical for disease development. Plots were irrigated using a mist irrigation system. Rating was performed by using two separate parameters, disease incidence and disease severity. Disease incidence is a percentage of plants infected. Disease severity is rated only on infected plants and it implies the extent to which plants are damaged by the fungal infection and potential yield loss.

In the field, the infection occurred at a late growth stage when plants are physiologically more tolerant to Sclerotinia. Therefore, there are no data on early infection. Disease severity is rated on the scale 1 to 9, where 1 is a dead, broken off plant and 9 is a plant with no symptoms of disease.

SCLEROTINIA RATING SCALE
1—Prematurely ripened or dead plant
3—Large lesion >30 mm, weak and girdled stem
5—Large lesion >30 mm, stiff and nearly girdled stem
7—Small lesion <30 mm, stiff and not girdled stem
9—No symptoms Intermediate scores can be assigned if symptom severity falls in between defined scores.

The results in Table 6 compare the greenhouse results with the field results.

genic plants of 164B1 in order to generate the F1s for the Sclerotinia screening.

The plasmid pPHP7746 was used to transform NSI 1565 to create 164B1. NS 1565 is a spring *Brassica napus* Pioneer variety which is registered as 46A65 in Western Canada. It is susceptible to Sclerotinia.

The experiment was arranged as RCBD (randomised complete block design) with two replications and 4 plants per replication. Plants were inoculated using the stem inoculation method with the isolate SS4. Plant tissue was sampled to estimate enzyme activity at the same time.

TABLE 6

Field reaction of the oxalate oxidase transgenic lines to Sclerotinia at Stirk's compared to indoor reaction to Sclerotinia and the level of enzyme activity

| Transgenic Entries and parental line | Field Disease Incidence (%) | Field Disease Severity 1 (1–9) | Field Disease Severity 2 (1–9) | Southern Analyses (# of copies) | Enzyme Activity T2 OD 550 nm | Indoor Screening Lesion length (mm) |
|---|---|---|---|---|---|---|
| 170B3 | 21.3 | 7.5+ | 6.5+ | 2 | 1.32 | 95.3 |
| 164B1 | 31.9 | 7.0+ | 5.0 | 1 | 1.31 | 80.9 |
| 17012 | 35.7 | 6.3 | 4.8 | 1 | 1.22 | 102.1 |
| 164C1 | 40.1 | 6.0 | 4.5 | 2 | N/A | N/A |
| 170J1 | 46.0 | 5.5 | 4.3 | 2 | 0.97 | 98.0 |
| NS1565 | 51.3 | 5.3 | 3.5 | 0 | 0.00 | 116.3 |

Table 6, shows a significant decrease in disease severity and incidence, especially ifn the field, that can be attributed to the oxalate oxidase's activity. The level of the enzyme activity is well correlated with disease incidence and severity.

The conclusion is that the oxalate oxidase gene in canola is efficient against Sclerotinia in the field, when compared against the non-transformed line NS1565. The transformed lines, especially those having a higher level of enzyme activity, exhibited a significant decrease in disease incidence and severity in the field when compared to the non-transformed line.

Combining Conventionally Tolerant Canola Lines with Oxalate Oxidase Expressors

In order to identify conventionally tolerant canola lines the stem isolation method of inoculating Sclerotinia was used. The fungus was grown on Potato Dextrose Agar (PDA). Agar plugs were cut (approximately 4–6 mm in diameter) using a cork borer. Plugs were taken from the outside ring of mycelium, before the colony reached the edge of the plate. Canola plants were inoculated at the onset of flowering to mid flowering. Stem inoculation was performed by attaching the plug to the stem (mycelial side on the stem) in a leaf axil approximately 10–12 cm above the soil level. Plants were incubated in the humidity chamber until symptoms started developing. Inoculum was then removed and the incubation in humidity was ceased when the lesion length on most of the plants of a susceptible check was at least 10–20 mm. Plants were moved to the greenhouse bench and lesion length was recorded. Lesion length development was observed after 10 days.

The conventionally tolerant line 96SN20002 is of canola quality and originates from of a recurrent selection program aimed at enhanced tolerance to Sclerotinia. Tolerant sources of canola quality that were used to establish the population were originated from the non-canola quality Asiatic germplasm lines: GP193 and JAP. The selection 96SN20002 was made by a single plant selections at Cycle 0—S2 generation (after S0 and S1 single plant selections) using the stem inoculation method. Sclerotinia tolerant F4 plants of 96SN20002 were crossed with Sclerotinia tolerant trans- A summary of the final lesion length rating and the oxalate oxidase activity can be found in Table 7.

TABLE 7

Summary of the final lesion length rating (millimeters) and oxalate oxidase activity of F1 TRANSGENIC/CONVENTIONAL Material, TOLERANT LINES and SUSCEPTIBLE CHECKS.

| Entries | Entry Name | Disease Severity (1–9) | Lesion Length Mm (Stem) | OX—OX Activity OD @ 550 nm* |
|---|---|---|---|---|
| 1 | Westar - susceptible | 2.2 | 101 | 0.1 |
| 2 | Quantum - susceptible | 1.2 | 98 | 0.1 |
| 3 | NS1565 - susceptible | 1.6 | 103 | 0.1 |
| 4 | F5 of 96SN20002 (conventionally tolerant) | 5.4 | 31 | 0.2 |
| 5 | 164B1 | 2.0 | 90 | 1.7 |
| 6 | QUANTUM/96SN20002 | 3.5 | 57 | 0.2 |
| 7 | QUANTUM/164B1 | 1.9 | 116 | 1.0 |
| 8 | NS1565/96SN20002 | 3.6 | 53 | 0.1 |
| 9 | NS1565/164B1 | 3.5 | 62 | 0.9 |
| 10 | 164B1/QUANTUM | 1.7 | 90 | 1.0 |
| 11 | 164B1/NS1565 | 2.2 | 102 | 0.9 |
| 12 | 96SN20002/QUANTUM | 3.7 | 45 | 0.1 |
| 13 | 96SN20002/NS1565 | 4.9 | 48 | 0.2 |
| 14 | 96SN2002/164B1 | 8.6 | 4 | 1.0 |
| 15 | 164B1/96SN20002 | 7.5 | 12 | 1.4 |

*Assay activity does not have background readings subtracted from values. (0.1~ background in this case)

The test was severe but it revealed the strength of conferred tolerance in the F1s between 164B1 and 96SN20002 and vice versa. This unusual reaction of elevated tolerance of the F1 is based on the interaction of different tolerances. It also appears that mechanisms of tolerance that are involved in this synergistic interaction are different. This level of tolerance was not observed in past greenhouse screening with either the conventional or transgenic material. It is important to note there are no canola quality lines tolerance to Sclerotinia presently available on the market.

The plasmid pPHP8188 was used to transform NS1565 to create the single copy transgenic line 156A. Sixty four independent pPHP8188 transformants were produced. Seventeen were single copy integration events. Transgenic progeny (T1) was selfed and (T2) homozygous seed identified for the seventeen lines via herbicide spraying. Oxalate oxidase assays were performed on the initial transgenics and again on several T2 plants from seven single copy lines which showed good expression at the T0 generation.

An indoor screening experiment using Sclerotinia was arranged as RCBD (randomised complete block design) with two replications and 4 plants per replication. Plants were inoculated using the stem inoculation method with the isolate SS4. Plant tissue was sampled to estimate enzyme activity at the same time.

A summary of the final lesion length rating and the oxalate oxidase activity can be found in Table 8.

TABLE 8 pPHP8188 transgenic and control Sclerotinia screening results.

| Entries | Vector (if applicable) | Disease Severity DS2 (Stem) Scale 1–9 | Lesion Length LL2 (Stem) mm | OX—OX Activity OD reading 550 nm |
|---|---|---|---|---|
| 185T | pPHP8188 | 1.5 | 129 | 0.06 |
| WESTAR | non trans* | 1.6 | 116 | 0.07 |
| NS1565-2 | non trans* | 1.5 | 117 | 0.08 |
| 185U | pPHP8188 | 1.7 | 115 | 0.11 |
| 186C | pPHP8188 | 2.2 | 97 | 0.13 |
| NS1565-1 | nontrans* | 2.3 | 103 | 0.15 |
| 96SN20139 | non trans convent source tolerance* | 4.2 | 45 | 0.15 |
| 153D | pPHP8188 | 4.6 | 51 | 0.46 |
| 185O | pPHP8188 | 4.5 | 65 | 0.47 |
| 153B | pPHP8188 | 3 | 86 | 0.48 |
| 185Q | pPHP8188 | 2.7 | 93 | 0.49 |
| 155F | pPHP8188 | 4.7 | 55 | 0.5 |
| 154A | pPHP8188 | 1.5 | 112 | 0.53 |
| 185W | pPHP8188 | 2.1 | 119 | 0.59 |
| 158F | pPHP8188 | 3.2 | 87 | 0.61 |
| 158D | pPHP8188 | 2.5 | 91 | 0.72 |
| 185I | pPHP8188 | 3.8 | 80 | 0.84 |
| F1 96SN20002/ 164B1 | convent source/ pPHP7746 | 6.7 | 22 | 1.09 |
| F1 164B1/ 96SN20002 | pPHP7746/ convent source | 6 | 37 | 1.2 |
| 156A | pPHP8188 | 3.6 | 82 | 1.52 |
| 164B1 | pPHP7746 | 4 | 63 | 1.8 |
| 170B3 | pPHP7746 | 5.5 | 48 | 1.9 |

*non-transgenic line.

Line 156A had the highest enzyme expression of the pPHP8188 lines but was still lower than the best pPHP7746 expressing lines 170B3 and 164B1. In the stem inoculation a correlation of 0.62 for disease severity/lesion length with enzyme activity is seen and indicates the transgenics exhibit tolerance to Sclerotinia. The test appears to be capable of generally separating very low enzyme activity vs. mid to high. Discrepancies are probably due to the low level of tolerance exhibited indoors indicating tests could not detect fine differences. Hybrid combinations were the strongest in terms of tolerance to Sclerotinia and the most consistent. Although, differences between the F1s (oxalate oxidase expressors and conventional) were not that great as in the pPHP7746 transgenics, it should be noted this is an interaction between plants and the fungus, and a pattern was observed.

Efficacy of Oxalate Oxidase Transgenic Canola Against Blackleg and Alternaria

Transgenic canola plants containing the oxalate oxidase gene were tested for resistance to two canola pathogens, Blackleg (*Phoma lingam*) and Alternaria. Disease severity and lesion length were similar for all plants regardless of oxalate oxidase activity. Therefore, expression of oxalate oxidase alone in canola does not confer resistance to Blackleg (*Phoma lingam*) or Alternaria.

Induction of Host Defenses in Oxalate Oxidase Transgenic Canola

Transgenic canola plants expressing oxalate oxidase were tested for the presence of PR-1 protein, chitinase and glucanase by Western blot analysis as was done in sunflower plants. No expression of PR-1, chitinase or glucanase was found in transgenic canola plants expressing oxalate oxidase.

Conclusion

Sunflower and canola differ as to induction of the host defense systems, but are similar in their significant increase in resistance to Sclerotinia when a transgenic oxalate oxidase expressing plant is crossed into a conventionally tolerant background. The synergistic effect created by oxalate oxidase expression in a tolerant background holds true regardless of the species of plant. Both canola and sunflower oxalate oxidase expressing plants in a tolerant background have surprising levels of resistance to Sclerotinia and little to none of the disease lesion mimic phenotype.

Example 3

Soybean

Soybean transgenics were produced by cocultivation of soybean cotyledonary node with Agrobacterium. This was done in accordance with the protocol defined by U.S. Pat. No. 5,563,055, and hereby incorporated by reference. The *A. tumefaciens* strain LBA4404 harboring binary plasmid p11144 which has supermas::oxalate oxidase and a histone promoter from Arabidopsis (2XH4) driving NPT was used to transform the soybean cotyledonary node. After culture on kanamycin containing media to provide a selective advantage to the transformed cells plants were regenerated. The resulting plants were screened by oxalate oxidase enzyme assay. Several plants with oxalate oxidase activity were obtained from each of three elite Pioneer soybean varieties (9151,92B52 and 9341). The activity is present in both leaf and stem tissue. The plants are characterized, enzyme rate are developed and PR protein induction estimates are done. Each event is selfed and homozygous lines are developed. Some crossing to Scerlotinia resistant and sensitive lines is also done. Baseline Sclerotinia scores for each of the soybean genotypes are performed and each transgenic is evaluated for resistance to Sclerotinia.

Example 4

Maize

Maize Transformation

Maize transformation was accomplished by particle bombardment of immature embryos with DNA encoding the oxalate oxidase gene fused to the maize ubiquitin promoter (ubi) and potato proteinase inhibitor II (PINII) 3' region. Ears PHN46 (U.S. Pat. No. 5,567,861, filed Aug. 3, 1993) from both greenhouse and field nursery sources were surface sterilized in 25% commercial bleach solution containing 0.5% Micro detergent (Micro, International Products Corp., Burlington, N.J.) for 20 min. then rinsed twice in sterile distilled water. Immature embryos were excised from these ears and placed embryo axis side down on 604 medium (0.4×N6 basal salts, 0.6×N6 macronutrients, 16.6 mM $KNO_3$, 20 $\mu$M $AgNO_3$, 0.6× B5H minor salts, 0.6× B5H Na/Fe EDTA, 0.4× Eriksson's vitamins, 0.6× S&H vitamins, 0.5 $\mu$M Thiamine HCL, 17.2 mM L-proline, 0.03% casein hydrolysate, 2% sucrose, 0.06% glucose, 0.2% gelrite, 0.8 mg/l 2,4-D, 1.2 mg/l dicamba) 4–5 days prior to particle bombardment. Four hours prior to bombardment the embryos were transferred with the same orientation to 604S medium (604 medium with sucrose adjusted to 12%). Tungsten particles were prepared by first cleaning the particles by suspending them in 0.1 M $HNO_3$ and subjecting them to constant sonication on ice for 30 min. The tungsten particles are then rinsed with sterile double distilled H2O 1x, 100% ethanol 1x, then resuspended in sterile double distilled $H_2O$ prior to aliquoting at 15 mg/ml. Plasmid PHP10963 was cut with restriction enzyme to release a DNA fragment which contains two genes; ubi:: oxalate oxidase::PINII and ubi-::moPAT::PINII. A quantity of this DNA fragment was associated with the particles prior to bombardment by adding components to a microtube in the following volumes and order: 100 μl tungsten particles, 1 μg DNA/10 μl TE buffer, 100 μl 2.5 M $CaCl_2$, 5 μl 0.1 M spermidine. Each component is added to the tube while constantly mixing, the final mixture was sonicated briefly, and then mixed by vortex for an additional 10 min. Tubes were then centrifuged briefly and supernatants removed from the particles and discarded. Particle associated with DNA were then washed with 500 μl 100% ethanol, centrifuged for 30 s followed by removal of the wash, and resuspended in 100 μl 100% ethanol. This suspension was used to provide 10 μl aliquots which were pipetted on the macrocarriers following a brief sonication and about 2 min prior to bombardment. Particle bombardment was achieved using a Dupont PDS 1000 He particle acceleration device with 650 psi rupture discs. Following bombardment, the embryos remained on 604S medium for 3 d and were then transferred in the same orientation to 604A medium (604 medium with 3 mg/l bialophos) for 1 wk. After 1 wk on 604A the bombarded embryos are transferred to 604J (604A medium lacking proline and casein hydrolysate, and with reduced $AgNO_3$ to 5 uM) and subcultured every 2 wk.

Oxalate oxidase enzyme assays-Maize

Twelve maize T0 transformed plants representing at least 5 independent molecular integration events were tested for the presence of functional oxalate oxidase enzyme by using the same enzyme assay protocol as described for sunflower tissue except that fresh maize leaf tissue was used in every case. Four maize leaf punches were used per sample and the color development reaction was scaled up to a larger final volume of 600 μl. Results of the oxalate oxidase enzyme assay are shown in Table 9 below.

TABLE 9

Oxalate oxidase enzyme assay results from T0 maize transgenic leaf samples with non-transformed maize B73 as negative control and transgenic sunflower line (193870) as positive control.

| T0 Plant Code | Event | No. of Samples | Call | Color Development (Ave. OD550) |
|---|---|---|---|---|
| 725611 | 1 | 2 | Positive | 0.17 |
| 725609 | 1 | 2 | Positive | 0.74 |
| 725610 | 1 | 2 | Positive | 0.72 |
| 726371 | 1 | 2 | Positive | 0.70 |
| 726372 | 1 | 2 | Positive | 0.46 |
| 725605 | 3 | 2 | Positive | 1.44 |
| 725606 | 3 | 2 | Positive | 1.29 |
| 725607 | 3 | 2 | Positive | 1.10 |
| 726370 | 3 | 2 | Positive | 1.13 |
| 726368 | 7 | 2 | Negative | 0.00 |
| 719934 | 10 | 2 | Positive | 1.41 |

TABLE 9-continued

Oxalate oxidase enzyme assay results from T0 maize transgenic leaf samples with non-transformed maize B73 as negative control and transgenic sunflower line (193870) as positive control.

| T0 Plant Code | Event | No. of Samples | Call | Color Development (Ave. OD550) |
|---|---|---|---|---|
| 719933 | 22 | 2 | Negative | 0.01 |
| B73 (negative control) | na | 2 | Negative | 0.00 |
| SF (positive control) | na | 1 | Positive | 1.74 |

Positive calli are then regenerated by the following method. Positive lines are transferred to 288J medium (in one liter brought up to volume with distilled water: 4.3 g MS salts (GIBCO #1117-074), 0.1 g myo-inositol, 5 ml MS vitamin stock solution, 0.5 mg zeatin, 60 g sucrose, 3 g Gelrite, 0.5 mg indole acetic acid, 0.1 μM absissic acid plus selective agent if desired) to initiate plant regeneration. Following somatic embryo maturation (2–4 weeks), well-developed somatic embryos are transferred to 272V medium (in one liter brought up to volume with distilled water: 4.3 g of MS salts, 0.1 g myo-inositol, 5 mls MS vitamin stock, 40 g sucrose, and 6 g bacto-agar) for germination and transferred to the lighted culture room. Approximately 7–10 days later, developing plantlets are transferred to 272V medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

Regenerated plants expressing oxalate oxidase are then tested for oxalate oxidase activity as described earlier. Positive plants are next assayed for PR-1, chitinase, glucanase, 14-3-3 protein, and SA levels as described earlier. Positive T0 and T1 maize plants expressing oxalate oxidase are tested for resistance to stress inducers, such as fungal, viral, and bacterial diseases; environmental stress; and resistance to insects.

Example 5

Maize Transformation with Galactose Oxidase

Maize callus was bombarded, as described above, with a DNA fragment containing the galactose oxidase gene (pPHP12046, ubiquitin::optimized PAT::PINII/ ubiquitin::galactose oxidase::PINII). The galactose oxidase gene isolated from the Fusarium strain NRRL 2903 and cited in McPherson, et al., *J of Biol Chem* 267(12):8146–8152 (1992), and herein incorporated by reference, was used in the pPHP12046 construct. The resulting callus was tested for galactose oxidase activity as described below:

1. Disrupt the callus (approximately 20 mg) in 100 mM Na phosphate pH 7.0 plus 25 mM N-ethyl maleimide (0.5 ml). The tissue can be homogenized. One way of homogenizing the tissue is the use an apparatus for tissue preparation as described in U.S. patent application Ser. No. 08/713,507, filed on Sep. 13, 1996, and herein incorporate by reference.
2. Add galactose (25 mM), horseradish peroxidase (10 U/ml), Amplex Red™ (70 uM–Molecular Probes)–total volume=200 μl.
3. Incubate until color develops, can be 10 minutes to 4 hours, but preferably about 1 hour.

4. Centrifuge and decant supernatant.
5. Record absorbance at 572 nm.

One skilled in the art will recognize various ways of measuring the fluorescent Resourfin product that are different from the way described above, but which still remain within the spirit and scope of the invention. Also, the concentration of horseradish peroxidase may be varied from 0.5 about μl/ml to 20 about μl/ml, and the concentration of Amplex Red™ may vary from about 20 μM to about 200 μM, depending on the desired reaction time. Reaction volume and galactose concentration may vary depending again on desired reaction time. Tissue other than callus may also be used. For example, galactose oxidase activity can be detected in all plant parts, including but not limited to, roots, stems leaves, flowers, pollen, and seed. Again, these variations are common changes one skilled in the art would make and still remain within the spirit and scope of the invention. Chloroform may also be added after incubation with galactose, Amplex Red™, and horseradish peroxidase, in order to stop the reaction. For the example reaction as described above 100 μl of chloroform may be added before centrifugation.

The above described assay detects $H_2O_2$ generated by galactose oxidase through a horse radish peroxidase-mediated 1:1 reaction between $H_2O_2$ and Amplex Red (10-acetyl-3,7-dihydroxyphenoxazine) that generates highly chromophoric and fluorescent resorufin (Zhou, et al., Anal Biochem 253:162–168 (1997)). Unfortunately the assay described in the Zhou, et al. article could not be used to measure galactose directly in disrupted callus because of a reaction between Amplex Red and substances containing free sulfydryl groups which results in $H_2O_2$-independent color development. This limitation has been overcome by disrupting tissue in the presence of N-ethyl maleimide eliminating the free sulfhydryl groups (Haugaard, et al., Anal Biochem 116:341–343 (1981)). This is the first time a galactose oxidase assay has been applied using Amplex Red. Several other chromogens such as o-dianisidine (Tressel et al., Meth Enzymol 90:163–171 (1982)) have been employed along with horse radish peroxidase for detecting $H_2O_2$ generated by oxidase enzymes, but because of the high extinction coefficient of resorufin, Amplex Red Assay has proven to be a much more sensitive chromogen.

The results of the galactose oxidase assay on maize callus can be seen in FIG. 7. Galactose oxidase can be detected in maize callus.

Positive calli are then regenerated by the following method. Positive lines are transferred to 288J medium (in one liter brought up to volume with distilled water: 4.3 g MS salts (GIBCO #1117-074), 0.1 g myo-inositol, 5 ml MS vitamin stock solution, 0.5 mg zeatin, 60 g sucrose, 3 g Gelrite, 0.5 mg indole acetic acid, 0.1 μM absissic acid plus selective agent if desired) to initiate plant regeneration. Following somatic embryo maturation (2–4 weeks), well-developed somatic embryos are transferred to 272V medium (in one liter brought up to volume with distilled water: 4.3 g of MS salts, 0.1 g myo-inositol, 5 mls MS vitamin stock, 40 g sucrose, and 6 g bacto-agar) for germination and transferred to the lighted culture room. Approximately 7–10 days later, developing plantlets are transferred to 272V medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

Regenerated plants expressing galactose oxidase are then tested for levels of galactose oxidase activity as described earlier. Positive plants are next assayed for PR-1, chitinase, glucanase, 14-3-3 protein, and SA levels as described earlier. Positive T0 and T1 maize plants expressing galactose oxidase are tested for resistance to stress inducers, such as fungal, viral, and bacterial diseases; environmental stress; and resistance to insects.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

---

What is claimed is:

1. A method of increasing a plant's resistance to Sclerotinia, the method comprising crossing a transgenic plant containing an oxalate oxidase gene with a Sclerotinia tolerant plant of the same species; wherein said gene is linked to a heterologous promoter.

2. The method of claim 1, wherein the plant is selected from the group consisting of sunflower, canola, alfalfa, soybean, maize, sorghum, wheat, and rice.

3. A Sclerotinia resistant plant resulting from a cross between a transgenic plant transformed with an oxalate oxidase gene and a Sclerotinia tolerant plant of the same species; wherein said gene is linked to a heterologous promoter.

4. The plant of claim 3, wherein the plant is selected from the group consisting of sunflower, canola, alfalfa, soybean, maize, sorghum, wheat, and rice.

* * * * *